US006475983B1

United States Patent
Eid et al.

(12)

(10) Patent No.: US 6,475,983 B1
(45) Date of Patent: *Nov. 5, 2002

(54) WATER-SOLUBLE POLYPEPTIDES HAVING A HIGH AFFINITY FOR α AND β INTERFERONS

(75) Inventors: Pierre Eid, Paris; Ion Gresser, Paris; Georges Lutfalla, Paris; Francois Meyer, Villejuif; Knud Erik Mogensen, Paris; Michael Tovey, Paris; Gilles Uze, Paris, all of (FR)

(73) Assignee: Medisup International N.V., Curacao (AN)

( * ) Notice: Subject to any disclaimer, the term of this patent is extended or adjusted under 35 U.S.C. 154(b) by 0 days.

This patent is subject to a terminal disclaimer.

(21) Appl. No.: 07/971,834

(22) PCT Filed: Apr. 17, 1991

(86) PCT No.: PCT/FR91/00318

§ 371 (c)(1),
(2), (4) Date: Feb. 17, 1993

(87) PCT Pub. No.: WO92/18626

PCT Pub. Date: Oct. 29, 1992

(51) Int. Cl.$^7$ .................. A61K 38/00; C07K 14/00; C12P 21/06; C12P 21/04
(52) U.S. Cl. .................. 514/2; 530/350; 530/351; 435/69.1; 435/325; 435/7.21; 435/69.51; 435/69.7; 424/85.4; 424/143.1; 536/23.5
(58) Field of Search .................. 530/350, 351; 514/2; 536/23.5; 435/325, 7.21, 69.1, 69.7, 69.51; 424/85.4, 143.1

(56) References Cited

U.S. PATENT DOCUMENTS

| | | | | |
|---|---|---|---|---|
| 5,218,090 A | * | 6/1993 | Connors | 530/350 |
| 5,221,789 A | * | 6/1993 | Novick et al. | 530/350 |
| 5,395,760 A | * | 3/1995 | Smith et al. | 435/325 |
| 5,516,515 A | * | 5/1996 | Vellucci et al. | 424/184.1 |
| 5,621,077 A | * | 4/1997 | Novick et al. | 530/350 |
| 5,643,749 A | * | 7/1997 | Revel et al. | 435/69.1 |
| 5,731,169 A | * | 3/1998 | Morgensen et al. | 435/69.1 |
| 5,889,151 A | * | 3/1999 | Mogensen et al. | 530/350 |

FOREIGN PATENT DOCUMENTS

FR 2657881 8/1991

OTHER PUBLICATIONS

Han et al. J. Biol, Chem. 1999, vol. 274, pp. 10008–10013.*
Novick, D.; et al. (1994) cell 77: 391–400.*
Novick, D.; et al. (1993) Lymphohine Cytokine Res. 12(5): 381, abst. No. 280.*
EID, P. et al. (1990) Biochem Biophys, Acta 1034: 114–17.*
Bello, I.; et al. (1990) Biosis Database Record No. 93051414: Biotecnol Apl. 7(3): 290–300 (1990).*
Aguet, M. (1991) Br, J. Haem. 79 (Suppl. 1): 6–8.*
Symons, J. A.; et al. (1995) cell 81: 551–60.*
Domanski, P., et al. (1996) Cytokine Growth Factor Rev. 7(2): 143–451.*
Colamonici, O. R., et al. (1994) J. Biol. Chem. 269 (13): 9598–602.*
Russel—Harde, D., et al. (1995). J. Biol. Chem. 270 (44): 26033–6.*
Proceedings Of The National Academy Of Sciences Of USA. vol. 809, May 1983; Washington, US; pp. 2539–2543 Arnheiter et al. —Orientation of human leukocyte interferon molecule on its cell surface receptor: carboxyl terminus remains accessible to a monoclonal antibody made against a . . . (see whole document).
Cell, vol. 60, Jan. 1990, Cambridge, NA US; pp. 225–234; Uze et al. "Genetic transfer of functional human interferon alpha receptor into mouse cells: cloning and expression of its cDNA"(see whole document).
Proceedings Of The National Academy Of Sciences Of USA, vol. 80, Jun. 1983; Washington, US: pp. 3269–3272, Faltynek et al: "Characterization of an interferon receptor on human lymphoblastoid cell". (see whole document).

\* cited by examiner

*Primary Examiner*—Lorraine Spector
*Assistant Examiner*—Janet L Andres

(57) ABSTRACT

Water-soluble polypeptides having high affinity for interferons α and β; DNA sequences and expression cells; a preparation method therefor; drugs; compositions containing same; and uses thereof as a diagnostic agent or for producing antibodies.

31 Claims, 5 Drawing Sheets

Fig. 1A

```
                                              CTGCAGGGATCTGCGGCGGCTCCCAG

ATG ATG GTC GTC CTC CTG GGC GCG ACG ACC CTA GTG CTC GTC
MET MET Val Val Leu Leu Gly Ala Thr Thr Leu Val Leu Val

GCC GTG GGC CCA TGG GTG TTG TCC GCA GCC GCA GGT GGA AAA
Ala Val Gly Pro Trp Val Leu Ser Ala Ala Ala Gly Gly Lys

AAT CTA AAA TCT CCT CAA AAA GTA GAG GTC GAC ATC ATA GAT
Asn Leu Lys Ser Pro Gln Lys Val Glu Val Asp Ile Ile Asp

GAC AAC TTT ATC CTG AGG TGG AAC AGG AGC GAT GAG TCT GTC
Asp Asn Phe Ile Leu Arg Trp Asn Arg Ser Asp Glu Ser Val

GGG AAT GTG ACT TTT TCA TTC GAT TAT CAA AAA ACT GGG ATG
Gly Asn Val Thr Phe Ser Phe Asp Tyr Gln Lys Thr Gly MET

GAT AAT TGG ATA AAA TTG TCT GGG TGT CAG AAT ATT ACT AGT
Asp Asn Trp Ile Lys Leu Ser Gly Cys Gln Asn Ile Thr Ser

ACC AAA TGC AAC TTT TCT TCA CTC AAG CTG AAT GTT TAT GAA
Thr Lys Cys Asn Phe Ser Ser Leu Lys Leu Asn Val Tyr Glu

GAA ATT AAA TTG CGT ATA AGA GCA GAA AAA GAA AAC ACT TCT
Glu Ile Lys Leu Arg Ile Arg Ala Glu Lys Glu Asn Thr Ser

TCA TGG TAT GAG GTT GAC TCA TTT ACA CCA TTT CGC AAA GCT
Ser Trp Tyr Glu Val Asp Ser Phe Thr Pro Phe Arg Lys Ala

CAG ATT GGT CCT CCA GAA GTA CAT TTA GAA GCT GAA GAT AAG
Gln Ile Gly Pro Pro Glu Val His Leu Glu Ala Glu Asp Lys

GCA ATA GTG ATA CAC ATC TCT CCT GGA ACA AAA GAT AGT GTT
Ala Ile Val Ile His Ile Ser Pro Gly Thr Lys Asp Ser Val

ATG TGG GCT TTG GAT GGT TTA AGC TTT ACA TAT AGC TTA CTT
MET Trp Ala Leu Asp Gly Leu Ser Phe Thr Tyr Ser Leu Leu

ATC TGG AAA AAC TCT TCA GGT GTA GAA GAA AGG ATT GAA AAT
Ile Trp Lys Asn Ser Ser Gly Val Glu Glu Arg Ile Glu Asn

ATT TAT TCC AGA CAT AAA ATT TAT AAA CTC TCA CCA GAG ACT
Ile Tyr Ser Arg His Lys Ile Tyr Lys Leu Ser Pro Glu Thr

ACT TAT TGT CTA AAA GTT AAA GCA GCA CTA CTT ACG TCA TGG
Thr Tyr Cys Leu Lys Val Lys Ala Ala Leu Leu Thr Ser Trp
```

Fig.1B

```
AAA ATT GGT GTC TAT AGT CCA GTA CAT TGT ATA AAG ACC ACA
Lys Ile Gly Val Tyr Ser Pro Val His Cys Ile Lys Thr Thr

GTT GAA AAT GAA CTA CCT CCA CCA GAA AAT ATA GAA GTC AGT
Val Glu Asn Glu Leu Pro Pro Pro Glu Asn Ile Glu Val Ser

GTC CAA AAT CAG AAC TAT GTT CTT AAA TGG GAT TAT ACA TAT
Val Gln Asn Gln Asn Tyr Val Leu Lys Trp Asp Tyr Thr Tyr

GCA AAC ATG ACC TTT CAA GTT CAG TGG CTC CAC GCC TTT TTA
Ala Asn MET Thr Phe Gln Val Gln Trp Leu His Ala Phe Leu

AAA AGG AAT CCT GGA AAC CAT TTG TAT AAA TGG AAA CAA ATA
Lys Arg Asn Pro Gly Asn His Leu Tyr Lys Trp Lys Gln Ile

CCT GAC TGT GAA AAT GTC AAA ACT ACC CAG TGT GTC TTT CCT
Pro Asp Cys Glu Asn Val Lys Thr Thr Gln Cys Val Phe Pro

CAA AAC GTT TTC CAA AAA GGA ATT TAC CTT CTC CGC GTA CAA
Gln Asn Val Phe Gln Lys Gly Ile Tyr Leu Leu Arg Val Gln

GCA TCT GAT GGA AAT AAC ACA TCT TTT TGG TCT GAA GAG ATA
Ala Ser Asp Gly Asn Asn Thr Ser Phe Trp Ser Glu Glu Ile

AAG TTT GAT ACT GAA ATA CAA GCT TTC CTA CTT CCT CCA GTC
Lys Phe Asp Thr Glu Ile Gln Ala Phe Leu Leu Pro Pro Val

TTT AAC ATT AGA TCC CTT AGT GAT TCA TTC CAT ATC TAT ATC
Phe Asn Ile Arg Ser Leu Ser Asp Ser Phe His Ile Tyr Ile

GGT GCT CCA AAA CAG TCT GGA AAC ACG CCT GTG ATC CAG GAT
Gly Ala Pro Lys Gln Ser Gly Asn Thr Pro Val Ile Gln Asp

TAT CCA CTG ATT TAT GAA ATT ATT TTT TGG GAA AAC ACT TCA
Tyr Pro Leu Ile Tyr Glu Ile Ile Phe Trp Glu Asn Thr Ser

AAT GCT GAG AGA AAA ATT ATC GAG AAA AAA ACT GAT GTT ACA
Asn Ala Glu Arg Lys Ile Ile Glu Lys Lys Thr Asp Val Thr

GTT CCT AAT TTG AAA CCA CTG ACT GTA TAT TGT GTG AAA GCC
Val Pro Asn Leu Lys Pro Leu Thr Val Tyr Cys Val Lys Ala

AGA GCA CAC ACC ATG GAT GAA AAG CTG AAT AAA AGC AGT GTT
Arg Ala His Thr MET Asp Glu Lys Leu Asn Lys Ser Ser Val

TTT AGT GAC GCT GTA TGT GAG AAA ACA AAA CCA GGA AAT ACC
Phe Ser Asp Ala Val Cys Glu Lys Thr Lys Pro Gly Asn Thr

TCT AAA TGAGGTACC
Ser Lys
```

Fig. 2A

CTGCAGGGATCTGCGGCGGCTCCCAG

| | | | | | | | | | | | | |
|---|---|---|---|---|---|---|---|---|---|---|---|---|
| ATG | ATG | GTC | GTC | CTC | CTG | GGC | GCG | ACG | ACC | CTA | GTG | CTC | GTC
| MET | MET | Val | Val | Leu | Leu | Gly | Ala | Thr | Thr | Leu | Val | Leu | Val

```
ATG ATG GTC GTC CTC CTG GGC GCG ACG ACC CTA GTG CTC GTC
MET MET Val Val Leu Leu Gly Ala Thr Thr Leu Val Leu Val

GCC GTG GGC CCA TGG GTG TTG TCC GCA GCC GCA GGT GGA AAA
Ala Val Gly Pro Trp Val Leu Ser Ala Ala Ala Gly Gly Lys

AAT CTA AAA TCT CCT CAA AAA GTA GAG GTC GAC ATC ATA GAT
Asn Leu Lys Ser Pro Gln Lys Val Glu Val Asp Ile Ile Asp

GAC AAC TTT ATC CTG AGG TGG AAC AGG AGC GAT GAG TCT GTC
Asp Asn Phe Ile Leu Arg Trp Asn Arg Ser Asp Glu Ser Val

GGG AAT GTG ACT TTT TCA TTC GAT TAT CAA AAA ACT GGG ATG
Gly Asn Val Thr Phe Ser Phe Asp Tyr Gln Lys Thr Gly MET

GAT AAT TGG ATA AAA TTG TCT GGG TGT CAG AAT ATT ACT AGT
Asp Asn Trp Ile Lys Leu Ser Gly Cys Gln Asn Ile Thr Ser

ACC AAA TGC AAC TTT TCT TCA CTC AAG CTG AAT GTT TAT GAA
Thr Lys Cys Asn Phe Ser Ser Leu Lys Leu Asn Val Tyr Glu

GAA ATT AAA TTG CGT ATA AGA GCA GAA AAA GAA AAC ACT TCT
Glu Ile Lys Leu Arg Ile Arg Ala Glu Lys Glu Asn Thr Ser

TCA TGG TAT GAG GTT GAC TCA TTT ACA CCA TTT CGC AAA GCT
Ser Trp Tyr Glu Val Asp Ser Phe Thr Pro Phe Arg Lys Ala

CAG ATT GGT CCT CCA GAA GTA CAT TTA GAA GCT GAA GAT AAG
Gln Ile Gly Pro Pro Glu Val His Leu Glu Ala Glu Asp Lys

GCA ATA GTG ATA CAC ATC TCT CCT GGA ACA AAA GAT AGT GTT
Ala Ile Val Ile His Ile Ser Pro Gly Thr Lys Asp Ser Val

ATG TGG GCT TTG GAT GGT TTA AGC TTT ACA TAT AGC TTA CTT
MET Trp Ala Leu Asp Gly Leu Ser Phe Thr Tyr Ser Leu Leu

ATC TGG AAA AAC TCT TCA GGT GTA GAA GAA AGG ATT GAA AAT
Ile Trp Lys Asn Ser Ser Gly Val Glu Glu Arg Ile Glu Asn

ATT TAT TCC AGA CAT AAA ATT TAT AAA CTC TCA CCA GAG ACT
Ile Tyr Ser Arg His Lys Ile Tyr Lys Leu Ser Pro Glu Thr

ACT TAT TGT CTA AAA GTT AAA GCA GCA CTA CTT ACG TCA TGG
Thr Tyr Cys Leu Lys Val Lys Ala Ala Leu Leu Thr Ser Trp
```

Fig. 2B

```
AAA ATT GGT GTC TAT AGT CCA GTA CAT TGT ATA AAG ACC ACA
Lys Ile Gly Val Tyr Ser Pro Val His Cys Ile Lys Thr Thr

GTT GAA AAT GAA CTA CCT CCA CCA GAA AAT ATA GAA GTC AGT
Val Glu Asn Glu Leu Pro Pro Pro Glu Asn Ile Glu Val Ser

GTC CAA AAT CAG AAC TAT GTT CTT AAA TGG GAT TAT ACA TAT
Val Gln Asn Gln Asn Tyr Val Leu Lys Trp Asp Tyr Thr Tyr

GCA AAC ATG ACC TTT CAA GTT CAG TGG CTC CAC GCC TTT TTA
Ala Asn MET Thr Phe Gln Val Gln Trp Leu His Ala Phe Leu

AAA AGG AAT CCT GGA AAC CAT TTG TAT AAA TGG AAA CAA ATA
Lys Arg Asn Pro Gly Asn His Leu Tyr Lys Trp Lys Gln Ile

CCT GAC TGT GAA AAT GTC AAA ACT ACC CAG TGT GTC TTT CCT
Pro Asp Cys Glu Asn Val Lys Thr Thr Gln Cys Val Phe Pro

CAA AAC GTT TTC CAA AAA GGA ATT TAC CTT CTC CGC GTA CAA
Gln Asn Val Phe Gln Lys Gly Ile Tyr Leu Leu Arg Val Gln

GCA TCT GAT GGA AAT AAC ACA TCT TTT TGG TCT GAA GAG ATA
Ala Ser Asp Gly Asn Asn Thr Ser Phe Trp Ser Glu Glu Ile

AAG TTT GAT ACT GAA ATA CAA GCT TTC CTA CTT CCT CCA GTC
Lys Phe Asp Thr Glu Ile Gln Ala Phe Leu Leu Pro Pro Val

TTT AAC ATT AGA TCC CTT AGT GAT TCA TTC CAT ATC TAT ATC
Phe Asn Ile Arg Ser Leu Ser Asp Ser Phe His Ile Tyr Ile

GGT GCT CCA AAA CAG TCT GGA AAC ACG CCT GTG ATC CAG GAT
Gly Ala Pro Lys Gln Ser Gly Asn Thr Pro Val Ile Gln Asp

TAT CCA CTG ATT TAT GAA ATT ATT TTT TGG GAA AAC ACT TCA
Tyr Pro Leu Ile Tyr Glu Ile Ile Phe Trp Glu Asn Thr Ser

AAT GCT GAG AGA AAA ATT ATC GAG AAA AAA ACT GAT GTT ACA
Asn Ala Glu Arg Lys Ile Ile Glu Lys Lys Thr Asp Val Thr

GTT CCT AAT TTG AAA CCA CTG ACT GTA TAT TGT GTG AAA GCC
Val Pro Asn Leu Lys Pro Leu Thr Val Tyr Cys Val Lys Ala

AGA GCA CAC ACC ATG GAT GAA AAG CTG AAT AAA AGC AGT GTT
Arg Ala His Thr MET Asp Glu Lys Leu Asn Lys Ser Ser Val

TTT AGT GAC GCT GTA TGT GAG AAA ACA AAA CCA GGA AAT ACC
Phe Ser Asp Ala Val Cys Glu Lys Thr Lys Pro Gly Asn Thr

TCT AAA ATT TGG CTT ATA GTT GGA ATT TGT ATT GCA TTA TTT
Ser Lys Ile Trp Leu Ile Val Gly Ile Cys Ile Ala Leu Phe
```

Fig. 2C

```
GCT CTC CCG TTT GTC ATT TAT GCT GCG AAA CTC TTC TTG AGA
Ala Leu Pro Phe Val Ile Tyr Ala Ala Lys Val Phe Leu Arg

TGC ATC AAT TAT GTC TTC TTT CCA TCA CTT AAA CCT TCT TCC
Cys Ile Asn Tyr Val Phe Phe Pro Ser Leu Lys Pro Ser Ser

AGT ATA GAT GAG TAT TTC TCT GAA CAG CCA TTG AAG AAT CTT
Ser Ile Asp Glu Tyr Phe Ser Glu Gln Pro Leu Lys Asn Leu

CTG CTT TCA ACT TCT GAG GAA CAA ATC GAA AAA TGT TTC ATA
Leu Leu Ser Thr Ser Glu Glu Gln Ile Glu Lys Cys Phe Ile

ATT GAA AAT ATA AGC ACA ATT GCT ACA GTA GAA GAA ACT AAT
Ile Glu Asn Ile Ser Thr Ile Ala Thr Val Glu Glu Thr Asn

CAA ACT GAT GAA GAT CAT AAA AAA TAC AGT TCC CAA ACT AGC
Gln Thr Asp Glu Asp His Lys Lys Tyr Ser Ser Gln Thr Ser

CAA GAT TCA GGA AAT TAT TCT AAT GAA GAT GAA AGC GAA AGT
Gln Asp Ser Gly Asn Tyr Ser Asn Glu Asp Glu Ser Glu Ser

AAA ACA AGT GAA GAA CTA CAG CAG GAC TTT GTA TGA
Lys Thr Ser Glu Glu Leu Gln Gln Asp Phe Val

CCAGAAATGAACTGTGTCAAGTATAAGGTTTTTCAGCAGGAGTTACACTGGTACC
```

WATER-SOLUBLE POLYPEPTIDES HAVING A HIGH AFFINITY FOR α AND β INTERFERONS

The present invention relates to new water-soluble polypeptides, DNA sequences, new cells, the preparation process of said polypeptides, their use as medicaments and the compositions containing them.

α and β interferons form a group of secreted proteins endowed with diverse biological properties and characterized by their ability to induce, in the cells of vertebrates, an antiviral and anti-proliferative state (I. Gresser and M. G. Tovey, Biochem. Biophys. Acta 516:23/1978).

α interferon has significant effects on the immune, cellular and humoral system, in particular on the polyclonal activation of B cells (M. Peters, J. Immunol., 137:3153/1986), the inhibition of the T cell functions (J. Knop et al, J. Immunol., 133:2412/1984) and the modification of the expression of histocompatibility antigens (M. Fellous et al, Eur. J. Immunol., 9:446/1979). All these processes are involved in the development of auto-immunity.

Although interferon is considered as a beneficial factor for the organism, an abnormal production of interferon may contribute to the pathology of certain illnesses and in fact is associated with various so-called auto-immune illnesses. For example, high levels of interferon are present in the serum or tissues of patients suffering from various illnesses, such as lupus erythematosus, rheumatoid arthritis, Behcet's syndrome, diabetes mellitus, multiple sclerosis, aplasia of the marrow and a serious multiple immuno-deficiency illness. A direct correlation exists between the levels of this interferon and the poor prognosis of the development of the AIDS illness (E. Buimovivi-Klein et al; AIDS Res., 2:99/1986).

It has been shown that in a specific mouse strain (NZB) suffering from a spontaneous illness, which illness serves as an animal model of lupus erythematosus in man, the administration of α or β interferon aggravates the progression of the illness (H. Heremans et al, Infect. immun., 21:925/1978; C. Adam et al, Clin. Exp. Immunol., 40:373/1980).

In young mice, the administration of large quantities of interferon induces a growth-inhibition syndrome, necrosis of the liver and death (I. Gresser et al, Nature, 258:76/1975). Also, infection by certain viruses (such as the viruses of Pichinde lymphocytic choriomeningitis, or rheovirus) during the neonatal period of the female mouse is accompanied by the production of large quantities of endogenic interferon which brings about the same lethal syndrome. The administration of an α or β anti-interferon antibody protects the young mice infected at birth by the viruses of this syndrome mentioned above (Y. Riviere et al, Proc. Natl. Acad. Sci. USA, 74:2135/1977; Y. Riviere et al, J. Exp. Med., 152:633/1980; T. Clark et al, J. Virol, 59:728/1986). This experiment represents a convincing argument for the harmful role of interferon in the pathogenesis of this illness.

Furthermore, the activation of NK cells and the modification of the expression of histocompatibility antigens are both regulated by α or β interferon and play an important role in the rejection of bone marrow grafts (C. Ohien et al, Science, 246:66/1989). In fact, it was demonstrated that the production of α or β interferon is one of the essential elements in the resistance of F1 hybrid mice to a graft of the parental marrow (Afifi et al, J. Immunol., 134:3739/1985). Thus the treatment of F1 mice or also of allogenic mice by a murine α or β anti-interferon serum allows the grafting and proliferation of the parental or allogenic marrow (Afifi et al, 1985).

It is also known that the biological effects of interferons and their sub-types are generated by their interaction with a specific receptor which has a high affinity for the cell surface (M. Aguet et K. E. Mogensen, Academic Press, London, 1983).

At present no effective therapy exists for auto-immune illnesses and for other illnesses such as multiple sclerosis, which is suspected of having a connection with auto-immune illnesses. The present treatments for auto-immune type illnesses are unsatisfactory and have toxic effects. Those used in "anti-rejection" therapies inhibit the manifestations of these pathologies but not their causes and have a very high toxicity. It would therefore be highly desirable to have available medicaments having therapeutic effects and a reduced toxicity for auto-immune illnesses and organ rejections.

It would therefore be very desirable to block the action of (α or β) interferon by injection of an antagonist which in this way could be therapeutically beneficial for auto-immune type illnesses and for preventing the rejection of grafts. However, such an approach based on the injection of foreign immunoglobulin which has proved its effectiveness is not practical in a therapeutic treatment in man.

That is why the present Application relates to a new approach which is based on the use of a soluble form of the specific receptor of α interferon as antagonist to block the action of α or β interferon. These variants of the natural receptor, prepared by genetic engineering techniques, retain the ability to fix the endogenic α interferon either circulating or locally, and are deprived of the part which fixes them to the cell surface; they can circulate freely and due to their specificity only link up with α or β interferon.

By fixing α or β interferon, they are capable of blocking—as an antibody would—the action of α or β interferon in the organism.

It would therefore be desirable to have available a product capable of blocking the activity of α and/or β interferon.

That is why a subject of the present Application is a water-soluble polypeptide, characterized in that it has a high affinity for α and β interferons.

By "high affinity" is meant a dissociation constant of less than $10^{-9}$ M.

By "water-soluble" is meant that the said polypeptide is capable of circulating ,in an organism such as the human body then of fixing itself to a cell.

In the present Application, and in what follows, by "hybrid" is meant the product resulting from the fusion (or conjugation) of a water-soluble polypeptide according to the present invention ("soluble" part of the natural receptor, modified complete receptor, or "soluble" part of the natural receptor modified for example by substitution) and of another molecule, in particular of polypeptide type, such as an immunoglobulin or an immunoglobulin fragment.

By "soluble receptor of α and β interferons" (or of interferon) is meant one of the water-soluble polypeptides as defined above.

In order to simplify the wording, in what follows, "interferon receptor" will generally be referred to instead of "receptor for α and β interferons".

Among the polypeptides as defined above, a particular subject of the invention is a water-soluble polypeptide, characterized in that it corresponds to the formula given in annex 1.

This polypeptide corresponds to the extra-cellular soluble part of the natural native receptor of α or β interferon.

Of course polypeptides other than the polypeptide described above retain a high affinity for the said interferons. It is thus that the polypeptide given in annex 1 could be replaced in particular by substitution or deletion variants which are also part of the subject of the present Application.

With regard to the deletions, one or more amino acids of the polypeptide corresponding to FIGS. 1A–1B could be suppressed without unfavourably modifying the affinity vis-à-vis the α and β interferons.

Deletions could also relate to the complete and native receptor, in particular at the level of its soluble part, in such a way for example as to make it lose its ability to fix itself to the cell membrane and therefore make it available in the circulation.

If one starts with the sequence of the native and complete receptor of interferon given in annex 2, the trans-membrane and cytoplasmic sections of its sequence could for example be suppressed.

The deletion of the 437–457 residues corresponding to the trans-membrane region and the 458–557 residues (cytoplasmic region) will for example be carried out to obtain the soluble forms (circulatory).

The complete sequence of amino acids and nucleotides, coding for the complete receptor of α and β interferons is represented in annex 2.

In the case where deletions are carried out in the trans-membrane and cytoplasmic (or cellular and intra-cellular) sections, potentially immune epitopes can be avoided. One advantage of the native receptor α and β interferons whose trans-membrane region has been suppressed is its ability to be secreted in the supernatant of the culture medium of the recombinant host cells.

Therefore a subject of the present Application is water-soluble polypeptides, characterized in that they result from deletion of polypeptides corresponding to the formula of annex 1 or annex 2.

The substitution variants are also part of the subject of the present Application.

In this case, one or more amino acids in the sequence of the interferon receptor could be removed or replaced by others, the total number of amino acids being retained.

The substitutions will preferably relate to the soluble part of the interferon receptor. The substantial changes in the function or the immunological identity of the soluble part of the receptor will be carried out by selecting non-conservative substitutions as well as residues of amino acids or sequences which differ from those present originally on the polypeptide in a way which is most significant as regards their property of maintaining the three-dimensional structure of the polypeptide close to the substitution, of maintaining the conjugate or hydrophobicity of the molecule or most of the side chain.

The substitutions modifying most of the properties of the receptor are in particular those in which an amino acid residue, for example seryl or threonyl, is substituted by a hydrophobic residue, for example leucyl, isoleucyl, phenylalanyl, alanyl or valyl;

those in which a cysteinyl is replaced by any residue;

those in which a residue having an electropositive side chain, such as lysyl, arginyl or histidinyl residues, is replaced by an electronegative residue, for example glutamyl or aspartyl;

and those in which a residue having a bulky side chain, for example phenylalanyl, is replaced by a residue which does not have one.

The substitution variants may also relate to the structure of the complete interferon receptor and will relate in particular to its trans-membrane region. In fact, the substitutions at this level, by reducing the affinity of the said polypeptide for lipid cells or membranes, will produce a soluble form of the receptor of α and β interferons.

The trans-membrane section could be for example substituted by a different amino acid sequence, for example a homopoly-nucleotide DNA sequence or any sequence containing 5 to 50 identical amino acids, for example serine, lysine, arginine, glutamine and aspartic acid or other hydrophilic amino acids permitting the secretion of soluble receptors into the culture medium of the recombinant host cells.

Therefore a subject of the present Application is also water-soluble polypeptides, characterized in that they result from substitution of the pqlypeptides corresponding to the formula of annex 1 or annex 2.

The above information shows that both substitutions or deletions as well as combinations of such modifications could be carried out.

In a general way, the variants thus obtained will have no functional trans-membrane section and preferably will have no intra-cellular (cytoplasmic) part.

Other variants of the water-soluble polypeptides described above could be produced by chemical modification, in order in particular to improve the characteristics of the receptor of α and β interferons.

Such polypeptides could contain hydrophilic polymers such as polyethyleneglycol grafted onto their amino acids containing free amino groups such as lysine, or sulfhydryl groups such as cysteine.

These modifications could in particular give the polypeptides according to the present invention a higher half-life in plasma or also an increase in their solubility or finally a reduction of the immunogenic nature of the said polypeptides.

These modifications can be carried out by well-known methods such as for example those described in the U.S. Pat. No. 4,179,337.

A subject of the present Application is also the polypeptides described above, characterized in that they are hybridized (or also conjugated).

The conjugation can involve immuno-competent polypeptides, for example polypeptides which can cause an immune response in an animal to which the hybrid polypeptide is administered or which can link up with any antibody directed against the part of the polypeptide which does not correspond to the soluble interferon receptor.

In a general way, the epitopes which do not correspond to the said receptor will contain antigens recognized by the already-existing antibodies, for example polypeptide fragments of bacteria, such as betagalactosidase.

Immune conjugations can be carried out by cross-linking in vitro or by recombinant cell culture transformed by a DNA coding for an immunogenic polypeptide.

In the preferred conditions, the immunogenic agent will be inserted into or linked to the soluble receptor or a fragment derived from the soluble receptor by a polypeptide bond so as to obtain a linear polypeptide chain containing epitopes corresponding to the soluble receptor and at least one epitope foreign to the said receptor. These epitopes can be introduced into any other locus in the polypeptide chain compatible with the receptor or its fragments.

Such hybrids can be particularly useful when a formulation containing a pharmacologically acceptable support is administered to an animal with a view to the preparation of an antibody against the interferon receptor; these antibodies are themselves useful as diagnostic agents or for the purification of the native receptor or the soluble receptor of interferon.

Other conjugated polypeptides which can be immunogenic contain hybrids containing in addition to the water-soluble polypeptide that has been conjugated with the C-terminal region of a polypeptide according to the invention, a homopolymer such as a pentahistidine. The hybrid could then be easily isolated by using chelating agents such as zinc ions fixed to a support thus permitting the adsorption of the hybrid from impure mixtures and its elution. The soluble receptor can then be recovered for example by enzymatic cleavage.

Other hybrids can be produced to improve the secretion of the soluble receptor. A heterologous signal polypeptide replaces that of the soluble receptor and if the resultant hybrid is recognized by the host cell, it is used by the host cell and the receptor is secreted.

The selection of signal polypeptides can be carried out on the basis of the characteristics of the host cell used and can include sequences of bacteria, yeasts, fungi, plants, mammals or viruses.

In the preferred conditions, the polypeptides described above are conjugated with polypeptides, in particular possessing a structure adapted for slowing down their degradation in the human organism.

The hybridization in particular of plasma proteins having a plasma half-life greater than that of the soluble part of the receptor itself (usually greater than 20 hours for these plasma proteins) with a soluble polypeptide according to the present invention will permit the duration of action of the soluble polypeptide to be extended.

Such plasma proteins contain for example serum-albumin, apolipoproteins, transferrins and preferably immunoglobulins, in particular G type, and especially G1 type.

Preferably, such hybrids will not be immunogenic in the animal or man for whom they will be used and the said plasma proteins will also not bring about harmful side effects in patients due to their own habitual biological activity.

In the preferred implementation conditions, the water-soluble polypeptide according to the invention will be conjugated with an immunoglobulin, in particular at the level of its constant region. A preferred immunoglobulin will be of G type, in particular G1 type.

The immunoglobulins and some of their variants are known; many were prepared by recombinant cell culture (Kohler et al, PNAS, USA, 77, 2197 (1980); Morrison et al, Ann. Rev. Immunol. 2, 239 (1984)).

The polypeptides according to the present invention which have the activity of the extra-cellular part of the native receptor of α and β interferons can be conjugated by their C-terminal end to the N-terminal end of the constant region of the light chain or the heavy chain.

In this way the variable region can be replaced and at least the CH2 and CH3 transition region of the constant region of the heavy chain is retained in a functionally-active form.

For this the appropriate DNA sequence can be constructed and expressed in the recombinant culture cells.

The immunoglobulins and the other polypeptides having in particular a half-life in the plasma greater than that of the soluble receptor of the α and β interferons can be conjugated with the said receptor and with its variants according to the same process.

The extra-cellular part of the interferon receptor will contain at most 427 to 436 amino acids starting from the initial methionine (see annex 1).

Generally, the sequences containing the cell region including the fixation region will be conjugated with the sequence of the immunoglobulins.

The precise conjugation site is not critical. The boundaries indicated above are only to be considered as indications and other neighbouring sites for the soluble interferon receptor can be chosen with the aim of optimizing the secretion or the fixation characteristics of the soluble receptor of the α and β interferons. The optimum site could be determined by the usual experiments.

In general, it has been found that the hybrids are expressed in the cell, but with some variation in the degree of secretion of the recombinant host cells. The following table shows different immunoglobulin—interferon receptor fusions which were obtained:

(a) RCl (b) (RCl)2

(c) (RCh)2

(d) (RCl)2(RCh)2 in which "R" represents a part of the extra-cellular section of the soluble receptor of and interferons containing the fixation site and Cl and Ch represent the constant areas of the light chain and the heavy chain respectively of human immunoglobulin. The above structures represent the main structures only, for example they do not show the joint (J) region or other sections of the immunoglobulin, or the disulphide bridges. When such sections are necessary for binding activity, they must be present in the position that they occupy naturally in the soluble receptor of α and β interferons, immuno-receptor of α and β interferons or immunoglobulin.

These examples are representative for bifunctional hetero-antibodies containing different ligand-receptor sites where a VhCh immunoglobulin will be able to be linked with a predetermined antigen. More complex structures will result when using heavy chains of immunoglobulins of other classes, for example IgM, IgG2, 3, 4, IgA, IgE, IgD, but preferably IgG1.

A preferred hybrid results from the fusion of the N-terminal end of the soluble receptor of α and β interferons which contains the fixation site for the ligand of α and β interferons in the C-terminal part Fc of an antibody which contains the functions effecting immunoglobulin G1. Such examples are illustrated hereafter in the experimental part.

Such hybrids contain typically the first 436 amino acids or the first 427 amino acids of the soluble receptor of α and β interferons linked by their C-terminal end to the constant region of the K chain or the G1 chain. The DNA coding for the soluble receptor of α and β interferons described in annex 1 is synthesized by using a combination of the PCR reaction (Polymerase Chain Reaction: see R. K. Saiki et al, Science 239, 487–491 (1988)) and digestions by appropriate restriction enzymes as illustrated in the examples.

Complementary oligonucleotides were used in the cDNA sequence at the 5' end and at the predetermined sites downstream of the cDNA of the (a/b) IFN receptor on the basis of the sequence shown in annex 2.

As the template for the PCR reaction, a plasmid was used containing complete cDNA (Uzé et al) or a lambda bacteriophage. A commercially-available cDNA library can also be used; the cDNA fragment can also be synthesized directly from total RNA or from polyA+ RNA prepared according to well-known methods (see O. Ohara et al, PNAS 86, 5673–77 (1989), J. Delort et al, Nucl. Acid Res. 17, 6439–6448 (1989)). The CDNA or RNA library can be obtained from human cells such as Daudi, Namalwa or from organs such as the human spleen with essentially the same result.

The interferon receptor appears to be a unique polypeptide. Its sequence nevertheless has a certain allelic variation.

The DNA fragment is inserted into the DNA coding for the constant region of the light or heavy chain of an immunoglobulin; the latter will preferably be a human immunoglobulin if the fusion is intended for therapeutic treatments in man.

DNAs which code for immunoglobulins are known, can be obtained commercially or can be synthesized (see for example Adams et al, Biochemistry 19, 2711–2719 (1980); Gough et al, Biochemistry 19, 2702–2710 (1980); Dolby et al, PNAS USA 77, 6027–6031 (1980); Rice et al, PNAS USA 79, 7862–7865 (1982); Falkner et al, Nature 298, 286–288 (1982) and Morrison et al, Ann. Rev. Immunol. 2, 239–256 (1984)).

The DNAs which code for the hybrids will preferably be transfected into the host cells with a view to their expression. If the host already produces heavy immunoglobulin chains before transfection, it is then sufficient to transfect the soluble receptor hybrid of light chain α and β interferons, in order to produce a bifunctional hetero-antibody. Similarly, if the host cell already expresses a light chain, then the DNA which codes for the soluble receptor hybrid of heavy chain α and β interferons can be transfected in order to produce a bifunctional antibody. The bifunctional immunoglobulins which contain one or more chains containing is the fixation site of the α and β interferons and one or more chains containing variable regions are endowed with double specificity, namely vis-à-vis α and β interferons and vis-a-vis a predetermined antigen. These are produced by the processes mentioned above or by processes in vitro. In the latter case, for example, F(ab)2 fragments of the hybrid are prepared according to known methods (see for example the U.S. Pat. No. 4,444,878).

An alternative for producing bifunctional antibodies consists of fusing B cells or hybridomas which secrete antibodies having the specificity for a desired antigen with cells which produce hybrids of the soluble receptor for immunoglobulin α and β interferons, for example myelomas. The bifunctional antibodies can be recovered from culture supernatants of such hybridomas.

A subject of the present Application is DNA sequences, characterized in that they code for the water-soluble polypeptides described above or their hybrids in particular with polypeptides.

Examples of polypeptides having a high affinity for α and β beta interferons of mammals are for example the soluble receptors of α and β interferons of primates, the soluble receptors of human, murine, canine, feline, bovine, equine and porcine α and β interferons. These DNA sequences which code for these polypeptides have a certain number of uses. More particularly, these sequences or parts of sequences or their synthetic or semi-synthetic copies can be used to screen other cDNA libraries or human or animal genomic libraries to select by hybridization other DNA sequences which are similar to the soluble receptor ofα and β interferons. Such DNAs, their fragments or their synthetic or semi-synthetic copies represent variants of the soluble receptors of α and β interferons and can be used as the starting material for preparing other variants by mutation. Such mutations cannot change the sequence of amino acids coded by the mutated codons or on the contrary change the amino acids. The two types of mutations can be advantageous for the production or use of the soluble receptor of α and β interferons according to the present invention. These mutations can for example permit a high-level production, a simpler purification or a higher binding activity.

As an example of a DNA sequence, the sequence of the nucleotides from 1–1343 of annex 2 can be mentioned.

The DNA coding for the variants of the natural soluble receptor of α and β interferons will preferably be presented in a form which permits it to be expressed in a transcription unit under the control of control elements for transcription and translation of mammals, of micro-organisms or of viruses compatible with the envisaged host cell. After transformation, transfection or infection of appropriate cells, such vectors can permit the expression of the recombinant polypeptide. The variants of the natural soluble receptor of α and β interferons can be expressed in cells of mammals, yeasts, bacteria or other cells under the control of an appropriate promoter. Cloning and expression vectors for use with hosts of bacteria, fungi, yeasts or mammal cells are described by Pouwels et al, (Cloning Vectors: A laboratory manual, Elsevier, N.Y., 1985) the relevant parts of which are mentioned here by way of reference. The expression vector can, but does not have to, carry a replication site as well as one or more sequences of selection markers which permit selection in transformed cells.

The variations introduced into the DNA coding for the polypeptides described above must not change the reading frame and must not create complementary sequences which could produce secondary structures harmful to the expression.

The polypeptide variants of the natural soluble receptor of interferon will have approximately the same binding activity as the natural receptor, although it is possible to select the variants with a view to changing the characteristics of the receptor, for example in order to improve them, as indicated above.

Although the mutation site is fixed, the mutation itself is not. For example, to optimize the performance of a mutation at a given site, the codon or target region could be mutated at random and the polypeptide variants obtained screened with a view to finding the optimum combination of secondary activities. The techniques for introducing substitution mutations at given sites in a DNA are well known, for example the M13 system. The DNA coding for the human receptor can be obtained by any known process; its sequence appears in annex 2.

In general, prokaryotes are used to clone the polypeptide sequences described above, for example *E. coli* 294 (ATCC No. 31446) is particularly useful. Other strains can be used, in particular *E. coli* X 1776 (ATCC No. 31537).

The polypeptides according to the present invention can be expressed in cells of bacteria, yeasts, mammals or other types of cells, under the control of an appropriate promoter, for example prokaryote systems such as for example *E. coli* can be used to express the recombinant proteins of the present invention. *E. coli* is typically transformed by using a derivative of pBR322 (ATCC 37017) which is a plasmid derived from a strain of *E. coli* (Bolivar et al, Gene 2, 95 (1977)). pBR322 contains genes for resistance to ampicillin and tetracycline and, also, provides simple means for identifying the transformed cells. The plasmid pBR322 or other microbe plasmids must also contain, or be modified so as to contain, sequences for expression control commonly used in recombinant DNA constructions.

Such control elements include for example the lactose (lac) promoter (J. Mol. Appl. Genet., 1, 139–147 (1981)) available under the No. ATCC 37121, the β-lactamase promoter (Chang et al, Nature 275, 615 (1978)), the tryptophan promoter (Miozzari J. Bact. 133, 1457–1466 (1978) and hybrid promoters such as tac (H. de Boer et al, PNAS USA 80, 21–25 (1983)) available under the No. ATCC 37138. Other representative but non-limitative examples are commercial vectors such as for example pKK223-3 which contains the trc or pPL-lambda promoter which contains the phage lambda promoter and the thermolabile repressor cI857 (Pharmacia Fine Chemicals, Uppsala, Sweden).

Other functional promoters are suitable. The DNA sequences are generally known; thus they can be conjugated with a DNA coding for a variant of the soluble receptor of α and β interferons using appropriate binders or adapters. The promoters for the bacterial systems contain in addition a so-called Shine-Dalgarno (SD) sequence linked in an operative way to the DNA coding for the antigen downstream.

Also a subject of the present invention is expression vectors for producing useful quantities of variants of soluble receptor of purified α and β interferons.

After the transformation of a suitable host strain and the culture of the said host strain to a suitable culture density, the selected promoter is depressed by appropriate means (for example raising the temperature or chemical induction) and the micro-organisms are cultured again. The micro-organisms are typically collected by centrifuging, lysed by physical or chemical means and the extract is recovered for an additional purification.

The micro-organisms are fermented, for example in a 10-litre fermentor using maximum growth and aeration conditions and vigorous agitation. An anti-foam agent is preferably used. The cultures grow at 30° C. in the super-induction medium as described by Mott et al, PNAS USA 82, 88 (1985), derepression is carried out at a culture density which corresponds to an A600 absorption of 5 to 6 by raising the temperature to 42° C. and collection is carried out 2 to 20 hours, preferably 3 to 6 hours, after the temperature change. The mass of micro-organisms is firstly concentrated by filtration or by other means and then centrifuged at 10000 g for 10 minutes at 4° C., then rapid congealing of the pellet is carried out. Recombinant proteins produced in bacterial culture are isolated by extraction of the pellet followed by one or more stages of concentration, desalting or ion-exchange or exclusion chromatography.

The micro-organisms used for the expression of variants of the soluble receptor of α and β interferons can be lysed by any suitable method, including congealing-decongealing cycles, sonication, mechanical rupture or the use of chemical agents. The soluble receptor of α and β interferons has a certain tendency to form aggregates which can be reduced by carrying out extraction and purification in the presence of a detergent such as Tween 80 or Triton X100.

For water-soluble polypeptides according to the present invention having a DNA sequence which does not start with methionine, the initiation signal will result in an additional methionine amino acid upstream and which represents the N-terminal residue of the product. Although such products having an additional N-terminal methionine can be used directly in the compositions and the methods of the present invention, it is normally preferable to remove this methionine beforehand. Standard methods in this field are known for removing such N-terminal methionines either in vivo or ex vitro.

Yeast systems, preferably using Saccharomyces types such as S. cerevisiae, commonly available, can also be used to express the polypeptides of the present invention.

In general, useful yeast vectors contain a replication origin and a selection marker allowing the transformation of the yeast as well as E. coli, for example the E. coli ampicillin resistance gene and the trpl gene of S. cerevisiae which provides a selection marker for a yeast mutant which cannot grow in tryptophan (available under ATCC No. 44076) and a promoter obtained from a gene superexpressed in the yeast to induce the transcription of a gene upstream. Appropriate promoter sequences for yeast hosts include the promoter of 3-phosphoglycerate kinase or other glycolysis enzymes, the promoter of acid phosphatase, for example PH05, the promoter of alpha type coupling factors. Other yeast promoters which can be used are promoter regions such as 2-alcoholdehydrogenase (Russell et al, J. Biol. Chem. 258, 2674, 1982). A signal peptide, for example the signal peptide of the factor allowing the secretion of a heterologous yeast protein can be inserted between the promoter and the structural gene to be expressed upstream (see Bitter et al, PNAS USA, 82, 5330, 1984). Yeast transformation methods are known to a man skilled in the art and a representative technique is described by Hinnen et al, PNAS USA 75, 1929 (1978) which permits trp+ transformants to be selected in a selection medium containing 0.67% nitrogenous yeast base, 0.5% Casamino acids, 2% glucose, 10 ug/ml uracil. Transformed host strains containing vectors having the PH05 promoter can be cultivated first in a preculture in a rich medium and subsequently depressed by reducing the concentration of inorganic phosphate in the medium. The strain is cultivated using conventional techniques.

The recombinant polypeptide is obtained by extraction of the cellular pellet which can be lysed either by enzymatic digestion with glucosidases followed by treatment with detergent or by mechanical forces such as for example the French press, followed by one or more stages of concentration, desalting, ion-exchange or exclusion chromatography. In the case where the polypeptide is secreted into the periplasmic space, it is recovered after treatment with chemical agents, for example EDTA which damages the outer layer of the membrane and which permits the release of the recombinant polypeptide. In the case where the polypeptide is secreted into the culture medium, it can be directly recovered.

Mammallian cells can also be used to express the polypeptides according to the present invention under the control of suitable promoters. Cell-free systems could also be used to produce soluble receptors of α and β interferons of mammals using RNAs derived from the DNA constructed by the present invention.

Promoters which control expression in mammalian host cells can be obtained from different sources, for example from virus genomes such as polyoma, simian Virus SV40, adenovirus, retrovirus, cytomegalovirus of hepatitis B or mammalian promoters, for example the promoter containing sites sensitive to DNAse I of the gene of human beta-globin or insect virus promoters such as the baculovirus system polyhedron promoter. For expression in animal cells, the control region derived from the late major promoter of adenovirus 2 is preferably used.

The early and late regions of SV40 are suitably isolated from the SV40 virus in the form of a restriction fragment which contains the replication origin of the virus (see Fiers et al, Nature 273, 113, 1978).

The early immediate region of the human cytomegalovirus is isolated in the form of a Hind IIIE restriction fragment (Greenaway P. J. et al, Gene 18, 3556360, 1982). The late promoter of the adenovirus-2 is isolated in the form of a Hind III restriction fragment containing the map units from 8 to 17 (S. Hu & J. L. Manley, Proc. Natl. Acad. Sciences (USA) 78, 820 to 824, 1981). Eukaryotic promoters of parent-type cellular origin are also useful.

In eukaryotic expression vectors, the transcription is increased by inserting, in addition to the promoter, sequences containing activators. The activators are DNA elements which act on the same side and which contain some 10 to 300 bp and increase the transcription initiation capacity of a promoter. Many of these activators are known for mammalian genes (globin, elastase, albumin, insulin, etc.). However, in general, activators of viruses infecting eukaryotic cells are used. Examples include the SV40 activator of the late side of the replication origin (100–270 bp), the activator of the early immediate promoter of cytomegalovirus, the activator of polyoma of the late side of the replication origin and the activator of adenovirus. The expression vectors used in the eukaryotic cells (yeasts, fungi, insects, plants, animal, human) can also contain sequences necessary for splicing and for termination of the transcription of factors which can influence the expression of mRNA. Expression vectors will contain a selection gene.

Examples of selection markers for mammalian cells are dehydrofolate reductase (DHFR), thymidine kinase or neomycin. When such selection markers are transfected into a host mammalian cell, the transformed cell can survive if it is put under selection pressure. In general, two types of selection systems are used. On the one hand, the use of a mutant line whose growth is dependent on a medium supplemented with certain ingredients such as for example CHO DHFR-cells or murine LTK-cells. These cells are not capable of growing without the addition of thymidine or hypoxanthine and these cells survive if a functional DHFR or TK gene is introduced by transfection. Thus, the cells not transformed by the DHFR or TK gene will not grow in the non-supplemented medium.

In addition, dominant selection is used which does not require a mutant cell: for example the gene which makes the transfected cell resistant to a toxic substance is transfected and expressed (see Southern & Berg, J. Molec. Appl. Genet. 1, 327 (1982); Mulligan & Berg Science, 20, 1422 (1980); Sugden et al, Mol. Cell. Biol. 5, 410–413 (1985).

The increase or the replication of certain chromosome regions of the cell is called amplification and can be brought about by using a selection agent such as for example methotrexate (MTX) which inactivates the DHFR. The amplification or increase of copies of the DHFR gene result in a greater production of DHFR with higher quantities of MTX. The degree of amplification increases with the concentration of MTX in the culture medium. The amplification of a desired gene is obtained by cotransfection of the desired gene and of the DHFR gene which are cointegrated in the chromosome. After co-amplification of the desired gene and the DHFR gene, the gene which codes for the desired protein expresses more of the desired protein.

The preferred host cells for the expression of variants of the soluble receptor of interferon of the present invention are mammalian cells which include monkey kidney cells (COS-7, ATCC CRL 1651 and Chinese hamster cells, CHO-DHFR-, Urlaub & Chasin, PNAS (USA), 77, 4216, 1980).

Transformation methods for mammalian cells are well known and a preferred method is described by Graham F. & van der Eb (Virology 52, 456–457, 1973) using the precipitation of DNA with calcium phosphate. Another method is electroportation as described by G. Chu et al, Nucl. Acid. Res. 15, 1311–1326, 1987. Other transfection methods such as for example injection into the nucleus or fusion with protoplasts can also be used.

The construction of expression vectors containing the desired control and coding sequences are prepared using well-known standard methods (see for example Maniatis T. et al, Molecular Cloning, 133–134 Cold Spring Harbor 1982; Current Protocols in Molecular Biology, edited by Ausubel et al, 1987, published by Greene Publishing Associates & Wiley-Interscience). The plasmids or fragments of DNA isolated are cut, sized and spliced again into the desired form.

The correct plasmid sequences are determined after transformation with ligation mixtures in E. coli HB101 or E. coli K12 294 (ATCC 31446). The transformants resistant to ampicillin are selected. The plasmids are isolated from the transformants and analyzed by restriction enzymes or by determination of the sequences by well-known methods (see Messing et al, Nucl. Acid Res. 9, 309 (1981) or Maxam et al, Methods in Enzymology 65, 499 (1980).

In general, the host cells are transformed by expression vectors, after which they are cultivated in an appropriate medium which contains substances for inducing the expression of the promoters, for selecting the transformants or for amplifying the genes. The culture conditions such as temperature, pH, etc. are those used for the selected culture for expression and are known to a man skilled in the art.

The polypeptides according to the present invention are isolated and purified from supernatants of recombinant host cells. Typically, the supernatants are concentrated by ultrafiltration, purified by ion-exchange chromatography or by immuno-affinity to adsorb the expected polypeptides and to subsequently elute them. The antigen has a great tendency to form aggregates. Thus, a detergent such as Tween 80, Triton X100 or CHAPS will advantageously be incorporated during purification. The final product will be stabilized with a protein such as albumin which may or may not contain a detergent.

It is however understood that all the vectors or sequences for controlling expression as well as all the host cells do not function in the same way for all the expression systems. However, a man skilled in the art will make a selection from these vectors, sequences for controlling expression and host cells, without moving outside the scope of the present invention. For example, single-cell hosts should be selected by considering their compatibility with the chosen vector, the toxicity of the product coded by the DNA sequences of the present invention, the secretion characteristics, their correct protein folding characteristics, their fermentation requirement and the ease of purification of the recombinant products after expression by the DNA sequences according to the present invention.

From these parameters, a man skilled in the art can select different vector system/expression control system/host cell combinations which express the DNA sequences according to the invention in fermentation or culture of animal cells on a large scale, for example CHO or COS-7 cells.

The polypeptides produced after expression of the DNA sequences according to the invention could be isolated from the fermentation or culture of animal cells and purified by a combination of conventional methods. A man skilled in the art will be able to select the most appropriate isolation and purification method without moving outside the scope of the present invention.

Also a subject of the present Application is cells, characterized in that they express a polypeptide described above and a preparation process for said polypeptides, characterized in that a cell capable of expressing the said polypeptide is cultivated in an appropriate nutritive medium.

The polypeptides according to the present invention are useful in particular as immunomodulators, quite particularly immuno-suppressants, and can be used in the treatment of auto-immune illnesses and graft rejections.

That is why a subject of the present Application is also medicaments, characterized in that they are constituted by water-soluble polypeptides as defined above.

Also a subject of the present Application is pharmaceutical compositions, characterized in that they contain as active ingredient one of the medicaments as defined above.

The purified polypeptides can be formulated in a pharmacologically acceptable conventional form. The constituents of this invention contain an immuno-therapeutically effective quantity of a polypeptide according to the present invention and a pharmaceutically acceptable support. The constituents according to the present invention can be presented in various forms: solid, semi-solid and liquid, in the form of tablets, pills, powder, injectable or infusable solutions. The preferred form depends on the administration method and the therapeutic use. In general, the pharmaceutical composition of the present invention will be administered using methods and compositions similar to those employed for other pharmaceutically important polypeptides. Thus, the polypeptide can be preserved in lyophilized form, reconstituted with sterilized water just before administration and administered by the usual routes, that it to say parenteral, sub-cutaneous, intravenous, intramuscular or intralesional. An effective dose may be of the order of 1 to 5 mg/kg of body weight/day. It is understood that a weaker or stronger dose exceeding twice the higher dose can be injected without harmful effects.

The medicaments according to the invention can be administered to patients in whom the abnormal production of α and β interferons is harmful, for example in illnesses such as lupus erythematosus, Behcet's syndrome, aplastic anaemia, diabetes mellitus, multiple sclerosis, rheumatoid arthritis or serious immuno-deficiency illnesses or to patients suffering from AIDS. Furthermore, the constituents according to the present invention, due to their ability to modify the immune activities such as activation of NK cells or expression of histocompatibility antigens, will also be administered as a therapeutic treatment to patients suffering from the rejection of organ grafts.

Due to their nature and their action mechanism, the compositions according to the present invention are free from general toxicity such as that of chemical immuno-suppressants such as glucocorticoids and therefore represent a great improvement relative to the medicaments in clinical use at present: for example immuno-suppressant substances or derivatives of such substances such as adrenal corticosteroids which inhibit cell division and the synthesis of cytokins for all the elements of the immune system or such as cyclosporin, a cyclic undecapeptide which selectively inhibits the activation of the immune system and represents an obvious improvement but which has a large number of non-immunological toxic effects (see N. Engl. J. Med., 321:25, 1725–1738, 1989).

The constituents according to the present invention can also be used to control agonists or antagonists which are different from α and β interferons.

The constituents according to the present invention in purified form are also useful for determining the tertiary structure of the fixation site of the soluble receptor of α and β interferons, a pre-condition for producing the molecular design in order to deduce from it the structures serving as a model for the synthesis of antagonists therapeutically useful as an immuno-suppressant agent or agonists useful as an anti-viral and anti-tumour agent.

Finally a subject of the present Application is therefore the use of a polypeptide as defined above, as a diagnostic agent, as well as the preparation of anti-α or β interferon antibodies.

The following examples illustrate the present invention without however limiting it.

EXAMPLE 1

Construction of vectors to express the soluble receptor of native α and β interferons and variants secreted by the latter in mammalian cells Section 1

Construction of plasmids for expressing native interferon.

DNA fragments containing complete c DNA and which code for the receptor of native α and β interferons were synthesized using the PCR reaction. A lambda ZAP bacteriophage which contains the complete length of the cDNA of the receptor of α and β interferons described in Annex 2 served as a template and specific oligonucleotides as primers for the reaction. In particular, the lambda ZAP bacteriophage was incubated with a pair of synthetic oligonucleotides consisting of an oligonucleotide complementary to the anti-sense strand at the 5' end of the cDNA and which has the sequence:

oligo 0:5'-CCGGCTGCAGGGATCTGCGGCGGCTCCCAG-3' and an oligonucleotide complimentary to the sense strand at the 3' end of the cDNA and which has the sequence:

oligo-1:3'-CAAAAAGTCGTCCTCAATGTGACCATGGCC-5'

The oligonucleotides are constructed in such a manner that after the PCR reaction is finished, the double strand DNA fragments obtained contain a restriction site for the restriction enzyme Pstl at the 5' end and Kpnl at the 3' end.

The PCR reaction was carried out in a reaction volume of 100 μl in a PCR buffer and containing primers at 1 mM each, 100 pg of lambda ZAP bacteriophage and 1 unit of Taq polymerase. The reaction conditions were as follows: 25 cycles, one cycle comprising an incubation at 95° C. for 1 minute (denaturation), 37–40° C. for 3 minutes (hybridization) then 72° C. for 4 minutes (polymerization). After the last cycle, the reaction was continued for 10 minutes at 72° C. and the samples were stored at 4° C. The reaction products were extracted with chloroform and after precipitation with ethanol the said products were digested by Kpnl and Pstl successively. The 1.7 kb fragment (fragment 1) was collected after electrophoresis on low melting-point agarose and linked to the expression vector pSVAdpA1.

pSVAdpA1 was constructed as follows:

The SV40 sequences were obtained form the pSV2DHFR plasmid (Subrami et al, Molec. Cell. Biol. 1, 854–864 (1981). They contain the replication origin, the activator and the early and late promoters (Pvull-HindIII fragment) and the intron of the t antigen surrounded by its splicing sites (donor and acceptor), as well as the polyadenylation site of the early region (Bg1 II-Eco RI fragment).

The late major promoter region of the 2-adeno was obtained from the pAdD26SVpA plasmid (EcoRI-PstI fragment) (Kaufman & Shimke, P. A., J. Mol. Biol. 159, 601–621 (1982)). It contains the promoter, the tripartite leader (Zain et al, Cell. 16, 851, 1979) and a hybrid splicing site which consists of a donor splicing site of 2-adeno and an acceptor splicing site of the variable region of an immunoglobulin.

A multiple cloning site is identical to that found in the pUC18 plasmid. It contains restriction sites for PstI, Sal I, Acc I, Hinc II, Xba I, Bam Hi, Xma I, Sma I, Kpnl, Sacl, Ban II, EcoRI.

The plasmid contains the replication origin of *E. coli* and the ampicillin resistance gene and was derived from the pML plasmid (Lusky & Botchan, Nature 293, 79–81, 1981).

pSVAd1 was digested with Kpn1 and Pst I successively, then treated with phosphatase and the fragment (fragment 2) which contains the major part of the plasmid was isolated by electrophoresis on low melting-point agarose. Fragment 2 was linked to fragment 1 and the fixation mixture was transfected into competent *E. coli* HB101 cells. The transformed culture was poured into Petri dishes containing ampicillin in their culture medium and the ampicillin resistant colonies were selected. From these transformants, the DNA plasmid was prepared and analyzed with restriction enzymes for the presence of the correct insert and by sequencing for the analysis of the junctions of the insert at the 5' and 3' ends to confirm that the sequence was correct.

The pSVAdIFRpA plasmid was used to express the native cell receptor in mammalian cells.

Section 2

Construction of plasmids to express secreted variants of α and β interferon receptors DNA fragments which contain different deletions of the receptor having different carboxyl terminals and which code for the secreted forms of the receptor were synthesized using the PCR reaction. More specifically, the lambda ZAP bacteriophage which contains the complete cDNA of the receptor was incubated with different pairs of synthetic oligonucleotides serving as fixers and which contain an oligonucleotide complementary to the anti-sense strand at the 5' end and having the sequence:

5' end oligo:
5'-CCGGCTGCAGGGATCTGCGGCGGCTCCCAG-3' and one of the following oligonucleotides complementary to the sense strand at different positions of the cDNA and which have the following sequences:

3' end oligo 1:
3'-GGTCCTTTATGGAGATTTACTCCATGGCC-5'
3' end oligo 2:
3'-TCACTGCGACATACACTCACTCCATGGCC-5'
3' end oligo 3:
3'-GTCAGACCTTTGTGCGGAACTCCATGGCC-5'
3' end oligo 4:
3'-GTCACACAGAAAGGAGTTTACTCCATGGCC-5'
3' end oligo 5:
3'-CTCTGATGAATAACAGATACTCCATGGCC-5'

The oligonucleotides are constructed so that after having completed the PCR reaction, the double strand DNA fragments obtained contain a restriction site for the restriction enzyme PstI at the 5' end and Kpn1 at the 3' end.

The PCR reaction was carried out in a reaction volume of 100 μl in a PCR buffer and contained primers at 1 μM each, 100 pg of lambda ZAP bacteriophage and 1 unit of Taq polymerase. The reaction conditions were as follows: 25 cycles, one cycle comprising an incubation at 95° C. for 1 minute (denaturation), 37–40° C. for 3 minutes (hybridization) then 72° C. for 4 minutes (polymerization). After the last cycle, the reaction was continued for 10 minutes at 72° and the samples were stored at 4° C. The reaction products were extracted with chloroform and after precipitation with ethanol the said products were digested with Kpn1 and Pstl successively. The desired fragments were collected after electrophoresis on low melting-point agarose. The lengths of the collected fragments were approximately the following:

reaction 1 (5' end oligo+3' end oligo 1): 1.3 kb fragment 3 reaction 2 (5' end oligo+3' end oligo 2): 1.3 kb fragment 4 reaction 3 (5' end oligo+3' end oligo 3): 1.1 kb fragment 5 reaction 4 (5' end oligo+3' end oligo 4): 0.9 kb fragment 6 reaction 5 (5' end oligo+3' end oligo 5): 0.6 kb fragment 7

The DNA fragments from 3–7 are each linked separately to the expression vector pSVAdpA1.

The pSVAd1 plasmid was digested with Kpn1 and Pst I successively, then treated with phosphatase and the fragment (fragment 2) which contains the major part of the plasmid was isolated by electrophoresis on low melting-point agarose. Then fragment 2 was linked separately to each of the fragments 3 to 7 and the fixation mixture was transfected into competent E. coli HB101 cells. The transformed cultures were poured into Petri dishes containing a growth medium, ampicillin, and the resistant colonies were selected. From these transformants, the DNA plasmid was prepared and analyzed by restriction enzymes for the presence of the correct insert and by sequencing for the analysis of the junctions of the insert at the 5' and 3' ends to confirm that the sequence was correct.

The plasmids were called pSVAdsIF1pA, pSVAdsIFR2pA, pSVAdsIFR3pA, pSVAdsIFR4pA, pSVAdsIFR5pA. They were used to express the soluble receptor and fragments of the soluble receptor in mammalian cells.

EXAMPLE 2

Expression in CHO cells

Once the transitory expression of the soluble receptor had been tested, the stable cell lines which express the soluble receptor in a continuous manner were established. To do this, the line deficient in dehydrofolate reductase: the CHO DUK-X line (F. Kao et al, PNAS USA, 64, 1284–91, 1969; Chasin L., & Urlaub G., Proc. Natl. Acad. Sci. 77, 4216–80, 1980) was used as host cell. By using this system, each of the constructions of the soluble receptor α of β and interferons was co-transfected with pSV2DHFR which contains the mouse DHFR gene (Subrami et al, Molec. Cell. Biol. 1, 854–864, 1981). Before carrying out this co-transfection, all the plasmids were linearized by restriction with a restriction enzyme and before the transfection, each plasmid was mixed separately with the pSV2DHFR plasmid so that the molar ratio of SV2DHFR to IFR plasmid was 1:10. This maximizes the number of copies of the IFR genes per transfectant. The plasmids are linked in the cell to form polymers which can be integrated in the chromosome of the host cell by recombination (Haynes & Weissmann, Nucl. Acids. Res. 11, 687–706, 1983; Scahill S. J. et al. Proc. Natl. Acad. Sci. USA, 80, 4654–58, 1983). The transfectants were selected which express the murine DHFR in an α-medium, a culture medium without nucleosides. Then methotrexate (MTX) (toxic analogue of folate which links to the DHFR) is added in order to select the cells which express high levels of DHFR. The resistance to MTX is due to a high expression of DHFR and is often the result of an amplification of the DHFR gene which can include long chromosome segments, called "amplified units" (Kaufman & Sharp, Molec. Cell. Biol. 1, 1069–1076, 1981). In this way the co-integration of DHFR sequences and soluble receptors of α and β interferons allows the amplification of the genes of soluble receptors of α and β interferons.

Cell lines transfected in a stable manner were isolated by cloning in a selective growth medium (DMEM/HAM F12 1:1 (Gibco)) supplemented with 10% foetal calf serum. Then, the clones were screened to find the one which expressed the most soluble receptors of α and β interferons by immunoprecipitation of the conditioned medium after labelling with $^{35}$S-cysteine in vivo. In particular, approximately $10^7$ CHO cells co-transfected either by pSVAdIFRpA or pSVAdsIFR1pA or pSVAdsIFR2pA or pSVAdsIFR3pA or pSVAdpA or pSV2DHFR were incubated for 5 hours at 37° C. with 100 mCi/ml of $^{35}$S-cysteine (Amersham) in 4 ml of RPMI cys-medium (Gibco). After the labelling of such cells, 1 ml of the filtered conditioned medium was adjusted with 0.5 mM of phenylmethylsulphonyl fluoride and immunoprecipitated as described hereafter. The precipitate was fractionated by electrophoresis in reducing conditions on a 7.5% PAGE gel (U. K. Laemmli, Nature, 227, 680–85, 1980).

EXAMPLE 3

Purification of the soluble receptor of α and β interferons

A clone of CHO cells which expresses the recombinant soluble receptor of α and β interferons of pSVAdsIFR3pA construction was selected and cultured in 4 roller bottles (Becton & Dickinson) in a DMEM/HAM F12 medium (1:1), supplemented with 1% FCS, 1 g/l of glucose and antibiotics such as streptomycin and penicillin (100 mg/ml) and 0.5 mM MTX for 8 days. The supernatant was collected, filtered through a 0.2 μm maxi dish (Gelman Sciences) and the secreted protein was concentrated on a FPLC mono Q anion exchange column (Pharmacia). The column is rinsed with a buffer containing 100 mM Hepes pH7, 10% glycerol, 1 mM phenylmethylsulphonyl fluoride (PMSF), 400 inhibition units of kallikrein/ml of aprotinin before being eluted with a discontinuous gradient of NaCl (from 0.2 to 1.0 M). The soluble receptor is capable of fixing the interferon and consequently the fixation of the interferon labelled with iodine 125 can be used to monitor the purification of the receptor.

The material containing the receptor is eluted through a dialyzed mono Q column and concentrated in a Micro-Prodicon type apparatus. A membrane which retains the proteins of molecular weight greater than 10,000 daltons is used. The concentrated material is deposited on a 3 mm gel of 7.5% polyacrylamide with 0.1% SDS. Concurrently, a sample (about 10 μg) is deposited to one side, on the same gel. After electrophoresis, this part of the gel is electro-transferred onto a polyvidinyl bifluoride membrane (Millipore) and then hybridized with recombinant human α 8 interferon labelled with iodine 125. In this way the position of the soluble receptor can be identified after electrophoresis. The part of the gel which contains the soluble receptor is then cut out and the protein collected by electro-elution, concentrated by molecular ultrafiltration and dialyzed in order to eliminate the SDS.

EXAMPLE 4

Construction of plasmids to express variants of soluble receptors of α and β interferons fused to the constant region of human kappa immunoglobulin and to the constant region of human gl immunoglobulin Fusions to the light chain Plasmids were constructed to express soluble receptors of α and β interferons having different lengths of extracellular region fused to the constant region of kappa immunoglobulin. These plasmids will be called hereafter pSVAdsIFR1K, pSVAdsIFR2K and pSVAdsIFR3K.

The pSVAdsIFR1K plasmid contains the N-terminal portion from the initiation codon for methionine up to the fusion 20 point which is after the codon for lysine 436, followed immediately by the sequence of the constant region of kappa immunoglobulin which starts at the codon for threonine 109 of the human kappa immunoglobulin (Kabat et al; Hieter, P. A. et al, Cell 22, 197–207, 1980).

Similarly, the pSVAdsIFR2K plasmid contains the N-terminal portion from the initiation codon for methionine up to the fusion point which is after the codon for glutamate 427, followed immediately by the sequence of the constant region of kappa immunoglobulin which starts at the codon for threonine 109 of human kappa immunoglobulin (Kabat et al; Hieter, P. A. et al, Cell 22, 197–207, 1980).

These plasmids were constructed as follows:

The DNA fragment of kappa immunoglobulin was synthesized from a human spleen cDNA library (Clontech Laboratories, Inc.). To synthesize the desired cDNA, oligonucleotides were used as a primer for the PCR reaction which have the sequence complementary to the predetermined regions, based on the published DNA sequence (Hieter, P. A. et al, Cell 22, 197–207, 1980). The 5' end oligonucleotide had the sequence:

5'-ACTGTGGCTGCACCATCTGTCTTCA-3' and that of the 3' end had the sequence:

3'-CCCTCTCACAATCTCCCTCCATGGCCAG-5'

The PCR reaction was carried out as described in Example 1, except that 1 μg of plasmid was used as a template and that after the reaction, the mixture was treated with Klenow polymerase in the presence of 4 triphosphate nucleosides to repair the ends of the two strands. The DNA was digested with the restriction enzyme Kpnl and the desired fragment was isolated by electrophoresis on low melting-point agarose.

The DNA fragments coding for the fragments of the soluble receptors of α and β interferons were synthesized in an identical manner. The 5' end oligonucleotide was the same as that described in Example 1, namely:

5'-CCGGCTGCAGGGATCTGCGGCGGCTCCAG-3' and the 3' end oligonucleotides were the following:

3'-CTCTTTTGTTTTGGTCCTTTATGGAGATTT-5' oligo 1

3'-TCGTCACAAAAATCACAGCGACATACACTC-5' oligo 2

3'-CCACGAGGTTTTGTCAGACCTTTGTGCGGA-5' oligo 3

The PCR reactions were carried out as described in Example 1, except that after the last reaction cycle, the 25 reaction products were treated with Klenow polymerase to repair the ends of the two strands and then with the restriction enzyme Pstl in order to obtain the IFR1, IFR2 and IFR3 fragments.

The expression vector pSVAdA1 was digested by Kpnl and Pstl successively followed by phosphatase and the P fragment containing the largest part of the plasmid was isolated by electrophoresis on low melting-point agarose.

In a reaction containing three components, the P fragment was linked to the immunoglobulin fragment and to the sIFR1 fragment. Similarly, the P fragment was linked to the immunoglobulin fragment and to the sIFR2 fragment and finally the P fragment was linked to the immunoglobulin fragment and to the sIFR3 fragment.

The ligation mixtures were each transformed separately into competent *E. coli* HB101 bacteria and the transformed cultures were poured into Petri dishes containing ampicillin in their culture medium and the ampicillin resistant colonies were selected. The plasmids were isolated from the transformants and analyzed with restriction enzymes to determine the insert or by sequencing to confirm the DNA sequence of the junction of the insert. These plasmids were used to express the fusions of the soluble receptor of α and β interferons.

Fusions of the heavy chain

Plasmids were constructed to express soluble receptors of α and β interferons having different lengths of extracellular region fused to the constant region of gl immunoglobulin. These plasmids will be called hereafter pSVAdsIFR1gl, pSVAdsIFR2gl and pSVAdsIFR3gl.

The pSVAdsIFR1gl plasmid contains the N-terminal portion from the initiation codon for methionine up to the fusion point which is after the codon for lysine 436, followed immediately by the sequence of the constant region of gl immunoglobulin which starts at the codon for alanine 113 of the human gl immunoglobulin (Kabat et al; Ellison J. W. et al, Nucl. Acids Res. 10, 4071–4079, 1982).

Similarly, the pSVAdsIFR2gl plasmid contains the N-terminal portion from the initiation codon for methionine up to the fusion point which is after the codon for glutamate 427, followed immediately by the sequence of the constant region of gl immunoglobulin which starts at the codon for alanine 113 of human gl immunoglobulin (Kabat et al; Ellison J. W. et al, Nucl. Acids Res. 10, 4071–4079, 1982).

The pSVAdsIFR3gl plasmid contains the N-terminal portion from the initiation codon for methionine up to the fusion point which is after the codon for proline 360, followed immediately by the sequence of the constant region of gl immunoglobulin which starts at the codon for alanine 113 of human gl immunoglobulin (Kabat et al; Ellison J. W. et al, Nucl. Acids Res. 10, 4071–4079, 1982).

These plasmids were constructed as follows:

The sequence coding for Gl immunoglobulin was synthesized from a human spleen cDNA library (Clontech Laboratories, Inc.). To synthesize the desired cDNA, oligonucleotides were used as a fixer for the PCR reaction which have the sequence complementary to the predetermined regions, based on the published DNA sequence (Ellison et al, Nucl. Acids Res. 10, 4071–4079, 1982). The 5' end oligonucleotide had the sequence:

5'-GCCTCCACCAAGGGCCCATCGGTCTTCCCC-3' and that of the 3' end had the sequence:

3'-GACAGAGGCCCATTTACTCACCATGGCCAG-5'

The PCR reaction was carried out as described hereafter:

The sIFR1, sIFR2 and sIFR3 fragments were the same as those described above and the expression vectors were constructed as described above regarding the fusion of the light chain.

EXAMPLE 5

Construction of vectors to express variants of the soluble receptor of α and β interferon in E. coli.

The pHR148 expression vector was used for the expression of sIFR in E. coli. pHR148 was described by Rink et al, Nucl. Acid. Res. 12, 6369–6387, 1984. The HR148 plasmid was digested successively by NcoI restriction enzymes followed by Klenow polymerase in the presence of 4 triphosphate nucleosides to repair the ends of the two strands and by KpnI. After treatment with phosphatase, the DNA fragment (fragment 1) which contains the largest part of the plasmid was isolated by electrophoresis on low melting-point agarose. The DNA fragment coding for the mature soluble receptor of α and β interferons, i.e. not having the peptide signal, was synthesized by the PCR reaction using the plasmid containing the complete cDNA (UZé et al, Cell.) as a template and a pair of oligonucleotides as a primer. The 5' end oligonucleotide (derived form the N-terminal region of the interferon) had the sequence:

5'-GGTGGAAAAAATCTAAAATCTCCTCAAAAAG-3' (oligo 1)

and the 3' end oligonucleotide (derived from the region which just precedes the transmembrane of the interferon) had the sequence:

3'-TCACTGCGACATACACTCATCCCATGGCC-5' (oligo 2)

The oligonucleotides were chosen in such a way that after PCR fusion, the synthesized fragment contains a KpnI restriction enzyme site at the 3' end and a "blunt" end at the 5' end.

The PCR reaction was carried out as described in Example 1, except that after the reaction the products were treated with Klenow polymerase to repair the ends of the two strands and then with the KpnI enzyme. The 1.3 kb fragment was isolated by electrophoresis on low melting-point agarose and ligated to fragment 1.

A second DNA fragment was synthesized in a similar manner, except that the 5' end oligonucleotide was replaced by the sequence:

5'-GGAAAAAATCTAAAATCTCCTCAAAAAG-3'

The ligation products were transformed in E. coli HB101 and the transformed cultures were poured into Petri dishes containing ampicillin in their culture medium. The ampicillin resistant colonies were selected and the plasmids were isolated from the transformants and analyzed by digestion with restriction enzymes and by sequencing to confirm the sequence at the fusion point of the insert.

These two plasmids called ptrpIFR1 and ptrpIFR2 were used to express the soluble receptor in E. coli. To express the recombinant protein, the transformants were placed in culture media of 20 to 50 ml in M9 medium (Rink et al, Nucl. Acid Res. 12, 6369–6387, 1984) to attain an absorption (A650) of 1.0. Then, the cells were centrifuged, washed and the soluble receptor of the interferon was extracted from the broken cells and purified. The soluble receptor of the α and β interferon was determined by Western blots or by dot blots as described hereafter.

EXAMPLE 6

Determination methods for the soluble receptor of human interferon

The determination methods for the soluble receptor are based on the capacity of the receptor to fix in a specific fashion the human α interferon.

a) Immunoprecipitation

The determination of the soluble receptor of human α and β interferons is based on the formation of a complex between the soluble receptor and the humano α 8 interferon labelled with iodine 125 which would prevent the fixing of $^{125}$I-IFN to a monoclonal antibody directed against the terminal amino part of a α 2 interferon (H. Arnheiter et al, Proc. Natl. Acad. Sci. (USA) 80:2539 [1983]). The terminal amino part of the molecule is not accessible to the antibody after fixing the interferon to its receptor (H. Arnheiter et al, [1983]). The $^{125}$I-IFN which remains free is complexed with the anti-IFN antibody then precipitated by the addition of the A-Sepharose protein (Pharmacia). The anti-IFN antibody is conjugated with the A protein according to the manufacturer's instructions.

Successive dilutions of the soluble receptors to be determined in 50 μl of borate buffer pH 8.3 (0.1M $H_3BO_3$, 0.025M $Na_2B_4O_7$, 0.075M NaCl, 0.1% NP4O) are mixed with a constant quantity (75 pmoles) of α 2 interferon labelled with iodine 125 with a specific activity of 81 Bq per fmole (K. E. Mogensen et G. Uze, Methods in Enzymol. 119C:267 [1986]) and incubated for one hour at 4° C. A constant quantity of A-anti-IFN protein is taken up in 50 μl volume, to which 50 μl of borate buffer pH 8.3 (0.2M $H_3BO_3$, 0.05M $Na_2B_4O_7$, 0.15M NaCl, 0.1% NP4O) is added. The mixture is agitated for one hour at 4° C. and then centrifuged in an Eppendorf-type micro-centrifuge at 10,000×g for 1 minute, and the supernatant is discarded. The precipitate is then washed six times with borate buffer pH 8.3 (0.1M $H_3BO_3$, 0.025M $Na_2B_4O_7$, 1M NaCl, 0.5% NP4O), twice with HEPES 40 mM pH 8 and 2% glycerol, then once with HEPES 40 mM pH 8 and 1M urea, and finally twice with HEPES 40 mM, pH 8. The radioactivity count of the immune complex in the precipitate will allow, by reference to the inhibition curve of the formation of the interferon-anti-interferon complex, determination of the quantity of soluble receptor of α and β interferons of the sample tested in this way.

b) Determination of the soluble receptor of human α and β interferons by inhibition of the fixing of the labelled interferon onto its cell receptor Successive dilutions of the soluble receptors of α and β interferons are incubated for 30 minutes at 4° C. with variable concentrations (0, 50, 100, 125, 500, 1000 and 2000 UI/ml) of recombinant human α 8 interferon labelled with iodine 125 (specific radioactivity 25 Bq per fmole). Then Daudi human lymphoid cells are added at a final concentration of $10^7$ cells/ml to different mixtures of $^{125}$I-IFN soluble receptor and incubated for two hours at 4° C. The cells are then centrifuged (800 g for 10 minutes) and the supernatant is discarded. They are washed three times with RPMI 1640 medium containing 0.5% foetal calf serum (Flow Laboratories) and the radioactivity bound to the cells is determined by counting with an LKB 1270-type gamma counter.

The quantity of soluble receptor of α and β interferons is determined from the inhibition curve of the specific binding of the interferon to its cell receptor. The specific binding is the difference between the binding curve of $^{125}$I-IFN only and that in the presence of a 100 times excess of non-labelled interferon).

c) Determination of the soluble receptor of α and β human interferons by "Western Blot"

The samples to be determined for the presence of the receptor of α interferon are concentrated by molecular ultrafiltration using an Amicon Centricon 30 type membrane which retains proteins of a molecular weight greater than 30,000 daltons. The samples are then taken up in a 60 mM Tris-HCl pH 6.8 buffer, 1.25% SDS, 1 mM PMSF and 400 inhibition units of kallikrein/ml of aprotinin and deposited on a gel of 7.5% polyacrylamide with 0.1% SDS. After electrophoresis under standard conditions, the samples are then transferred onto a polyvinidyl bifluoride membrane (Millipore) in a "semi-dry" type electrotransfer apparatus (Nova Blot, LKB) at 200 mA for one hour in a buffer of 39 mM of glycine, 48 mM tris-base pH 8.3 and 18% methanol. After the transfer, the membrane is treated with a buffer of 20 mM Tris-base, 0.2% Tween 20, pH 7.8 and 10% skimmed milk (Regilait, France) for 4 hours at 25° C. under agitation.

It is then hybridized with $^{125}$I-α 8 Interferon at $10^{-10}$M (specific activity 50 Bq per fentamole) for 2 hours at 25° C. under agitation in the same buffer. The membrane is then washed five times with aliquots of the same buffer, it is then air-dried and exposed to an X-ray sensitive film.

The recombinant human α 8 (α B) interferon is labelled with iodine 125 by a modification of the chloramine T method described previously (K. E. Mogensen et G. Uze, Methods in Enzymol. 119C:267 [1986]). This corresponds to a specific radioactivity of 25 Bq per fmole or 6 Bq per international unit of interferon.

d) Determination of the soluble receptor of human α and β interferons by "dot blot"

Successive dilutions of preparations of the soluble receptors to be determined are carried out in 50 μl of a buffer of 39 mM of glycine, 48 mM Tris-base pH 8.3 and deposited in the wells of a "Bio-Blot" type apparatus (Biorad) loaded with a polyvinidyl bifluoride membrane (Millipore).

The membrane is then treated for 4 hours at 25° C. under agitation with a buffer of 20 mM Tris-base, 0.2% Tween 20, pH 7.8 and 10% skimmed milk (Regilait, France). It is then hybridized with $^{125}$I-IFNα 8 at $10^{-10}$ M (specific activity 25 Bq per fmole) for 2 hours at 25° C. under agitation in the same buffer. Then, it is washed five times under agitation with aliquots of the same buffer and is exposed to an X-ray sensitive film. Analysis of the autoradiographs will allow, by reference to a standard curve, the determination of the quantity of $^{125}$I-IFN attached to the membrane and therefore from this to deduce the concentration of soluble receptor in the tested sample.

The recombined human α 8 (α B) interferon is labelled with iodine 125 by a modification of the chloramine T method (K. E. Mogensen and G. Uze, Methods in Enzymol. 119C:267 [1986]). This corresponds to a specific radioactivity of 25 Bq per fmole or 6 Bq per international unit of interferon.

EXAMPLE 7

Pharmaceutical composition

An injectable composition was prepared containing:

| | |
|---|---|
| the product of Example 3 | 100 mg |
| excipient for an injectable preparation | 2 ml |

What is claimed is:

1. An isolated polypeptide capable of binding to human α and β interferons, which polypeptide lacks a receptor transmembrane domain, wherein said polypeptide comprises an amino acid sequence selected from the group consisting of (a) SEQ ID NO:2, (b) SEQ ID NO:2 in which one amino acid is substituted or deleted, and (c) a fragment of (a) or (b) which is capable of binding to human α and β interferon.

2. The isolated polypeptide according to claim 1, comprising the amino acid sequence of SEQ ID NO:2.

3. The isolated polypeptide according to claim 1, comprising the amino acid sequence of SEQ ID NO:2 in which one amino acid is substituted or deleted.

4. The isolated polypeptide according to claim 1, wherein said polypeptide is a fragment of (a) or (b) which is capable of binding to human α and β interferon.

5. The isolated polypeptide according to claim 1, further comprising an amino acid sequence that provides the property of resisting the degradation in the human body of said polypeptide.

6. A pharmaceutical composition, comprising a polypeptide according to claim 1 as an active ingredient, and a pharmaceutically acceptable carrier or excipient.

7. A process for producing the polypeptide of claim 1,
culturing a host cell transformed with a nucleic acid encoding said polypeptide in a nutrient medium under conditions suitable for expressing the polypeptide; and
recovering the expressed polypeptide from the cell culture.

8. A hybrid protein, comprising a polypeptide according to claim 1, fused to an immunoglobulin.

9. The hybrid protein according to claim 8, wherein said immunoglobulin is IgG.

10. The hybrid protein according to claim 9, wherein said immunoglobulin is an $IgG_1$ immunoglobulin.

11. A process for producing the hybrid protein of claim 8 comprising:
culturing a host cell transformed with a nucleic acid encoding said hybrid protein in a nutrient medium under conditions suitable for expressing the hybrid protein; and
recovering the expressed hybrid protein from the cell culture.

12. An isolated polypeptide, consisting of the amino acid sequence of SEQ ID NO: 2.

13. A process for producing a polypeptide which lacks a transmembrane domain, wherein said polypeptide comprises the amino acid sequence of SEQ ID NO:2, comprising:
culturing a host cell transformed with a nucleic acid encoding said polypeptide in a nutrient medium under conditions suitable for expressing the polypeptide; and
recovering the expressed polypeptide from the cell culture.

14. An isolated DNA molecule, comprising a nucleotide sequence coding for the polypeptide according to claim 1, wherein said nucleotide sequence lacks a sequence encoding a receptor transmembrane domain.

15. The isolated DNA molecule according to claim 14 wherein said polypeptide is that having the amino acid sequence of SEQ ID NO:2 in which one amino acid is substituted or deleted.

16. The isolated DNA molecule according to claim 14, wherein said polypeptide is a fragment of (a) or (b) which is capable of binding to human α and β interferon.

17. Host cells transformed with the DNA molecule of claim 14.

18. An isolated DNA molecule in accordance with claim 14, wherein said polypeptide is that having the amino acid sequence of SEQ ID NO:2.

19. The isolated DNA molecule according to claim 18, wherein said nucleotide sequence corresponds to nucleotides 27 to 1334 of SEQ ID NO:1.

20. Host cells transformed with the DNA molecule of claim 18.

21. An isolated DNA molecule, comprising a nucleotide sequence coding for the hybrid protein of claim 8.

22. Host cells transformed with the DNA molecule of claim 21.

23. A method for preparing antibodies against interferon α and β receptor, comprising the steps of:
   administering a composition comprising the isolated polypeptide of claim 1, and a pharmacologically acceptable carrier, excipient, diluent, or auxiliary agent to an animal to raise antibodies against the isolated polypeptide;
   and recovering the antibodies raised against the isolated polypeptide from the animal or from antibody-producing cells derived from the animal.

24. A method for binding human α and/or β interferon, comprising contacting the polypeptide of claim 1 with human α and/or β interferon to thereby bind said polypeptide to said human α and/or β interferon.

25. A method in accordance with claim 24, for binding human α and β interferon comprising contacting said polypeptide with human α and β interferon.

26. A method in accordance with claim 24, for binding human α interferon comprising contacting said polypeptide with human α interferon.

27. A method in accordance with claim 24, for binding human β interferon comprising contacting said polypeptide with human β interferon.

28. A method for blocking the action of human α and/or β interferon in patients, comprising administering to a patient in need thereof a polypeptide in accordance with claim 1.

29. A method in accordance with claim 28 for blocking the action of human α interferon in patients, comprising administering said polypeptide to a patient in need thereof.

30. A method in accordance with claim 28 for blocking the action of human α and β interferon in patients, comprising administering said polypeptide to a patient in need thereof.

31. A method in accordance with claim 28 for blocking the action of human β interferon in patients, comprising administering said polypeptide to a patient in need thereof.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 1343 base pairs
      (B) TYPE: nucleic acid
      (C) STRANDEDNESS: single
      (D) TOPOLOGY: linear (ii) MOLECULE TYPE: cDNA (ix) FEATURE:
    (A) NAME/KEY: CDS
    (B) LOCATION: 27..1334

(xi) SEQUENCE DESCRIPTION: SEQ ID NO:1:

| | | | | | | | | | | | | | | | |
|---|---|---|---|---|---|---|---|---|---|---|---|---|---|---|---|
| CTGCAGGGAT | CTGCGGCGGC | TCCCAG | ATG | ATG | GTC | GTC | CTC | CTG | GGC | GCG | ACG | | | | 53 |
| | | | Met | Met | Val | Val | Leu | Leu | Gly | Ala | Thr | | | | |
| | | | 1 | | | | 5 | | | | | | | | |
| ACC | CTA | GTG | CTC | GTC | GCC | GTG | GGC | CCA | TGG | GTG | TTG | TCC | GCA | GCC | GCA | 101 |
| Thr | Leu | Val | Leu | Val | Ala | Val | Gly | Pro | Trp | Val | Leu | Ser | Ala | Ala | Ala |
| 10 | | | | 15 | | | | 20 | | | | | 25 | | |
| GGT | GGA | AAA | AAT | CTA | AAA | TCT | CCT | CAA | AAA | GTA | GAG | GTC | GAC | ATC | ATA | 149 |
| Gly | Gly | Lys | Asn | Leu | Lys | Ser | Pro | Gln | Lys | Val | Glu | Val | Asp | Ile | Ile |
| | | | 30 | | | | | 35 | | | | | 40 | | |
| GAT | GAC | AAC | TTT | ATC | CTG | AGG | TGG | AAC | AGG | AGC | GAT | GAG | TCT | GTC | GGG | 197 |
| Asp | Asp | Asn | Phe | Ile | Leu | Arg | Trp | Asn | Arg | Ser | Asp | Glu | Ser | Val | Gly |
| | | | | 45 | | | | 50 | | | | | 55 | | |
| AAT | GTG | ACT | TTT | TCA | TTC | GAT | TAT | CAA | AAA | ACT | GGG | ATG | GAT | AAT | TGG | 245 |
| Asn | Val | Thr | Phe | Ser | Phe | Asp | Tyr | Gln | Lys | Thr | Gly | Met | Asp | Asn | Trp |
| | | 60 | | | | | 65 | | | | | 70 | | | |
| ATA | AAA | TTG | TCT | GGG | TGT | CAG | AAT | ATT | ACT | AGT | ACC | AAA | TGC | AAC | TTT | 293 |
| Ile | Lys | Leu | Ser | Gly | Cys | Gln | Asn | Ile | Thr | Ser | Thr | Lys | Cys | Asn | Phe |
| | 75 | | | | | 80 | | | | | 85 | | | | |
| TCT | TCA | CTC | AAG | CTG | AAT | GTT | TAT | GAA | GAA | ATT | AAA | TTG | CGT | ATA | AGA | 341 |
| Ser | Ser | Leu | Lys | Leu | Asn | Val | Tyr | Glu | Glu | Ile | Lys | Leu | Arg | Ile | Arg |
| 90 | | | | | 95 | | | | | 100 | | | | | 105 |
| GCA | GAA | AAA | GAA | AAC | ACT | TCT | TCA | TGG | TAT | GAG | GTT | GAC | TCA | TTT | ACA | 389 |
| Ala | Glu | Lys | Glu | Asn | Thr | Ser | Ser | Trp | Tyr | Glu | Val | Asp | Ser | Phe | Thr |
| | | | | 110 | | | | | 115 | | | | | 120 | |
| CCA | TTT | CGC | AAA | GCT | CAG | ATT | GGT | CCT | CCA | GAA | GTA | CAT | TTA | GAA | GCT | 437 |
| Pro | Phe | Arg | Lys | Ala | Gln | Ile | Gly | Pro | Pro | Glu | Val | His | Leu | Glu | Ala |
| | | | 125 | | | | | 130 | | | | | 135 | | |
| GAA | GAT | AAG | GCA | ATA | GTG | ATA | CAC | ATC | TCT | CCT | GGA | ACA | AAA | GAT | AGT | 485 |
| Glu | Asp | Lys | Ala | Ile | Val | Ile | His | Ile | Ser | Pro | Gly | Thr | Lys | Asp | Ser |
| | | 140 | | | | | 145 | | | | | 150 | | | |
| GTT | ATG | TGG | GCT | TTG | GAT | GGT | TTA | AGC | TTT | ACA | TAT | AGC | TTA | CTT | ATC | 533 |
| Val | Met | Trp | Ala | Leu | Asp | Gly | Leu | Ser | Phe | Thr | Tyr | Ser | Leu | Leu | Ile |
| | 155 | | | | | 160 | | | | | 165 | | | | |
| TGG | AAA | AAC | TCT | TCA | GGT | GTA | GAA | GAA | AGG | ATT | GAA | AAT | ATT | TAT | TCC | 581 |
| Trp | Lys | Asn | Ser | Ser | Gly | Val | Glu | Glu | Arg | Ile | Glu | Asn | Ile | Tyr | Ser |
| 170 | | | | | 175 | | | | | 180 | | | | | 185 |
| AGA | CAT | AAA | ATT | TAT | AAA | CTC | TCA | CCA | GAG | ACT | ACT | TAT | TGT | CTA | AAA | 629 |
| Arg | His | Lys | Ile | Tyr | Lys | Leu | Ser | Pro | Glu | Thr | Thr | Tyr | Cys | Leu | Lys |
| | | | | 190 | | | | | 195 | | | | | 200 | |
| GTT | AAA | GCA | GCA | CTA | CTT | ACG | TCA | TGG | AAA | ATT | GGT | GTC | TAT | AGT | CCA | 677 |
| Val | Lys | Ala | Ala | Leu | Leu | Thr | Ser | Trp | Lys | Ile | Gly | Val | Tyr | Ser | Pro |
| | | | 205 | | | | | 210 | | | | | 215 | | |
| GTA | CAT | TGT | ATA | AAG | ACC | ACA | GTT | GAA | AAT | GAA | CTA | CCT | CCA | CCA | GAA | 725 |
| Val | His | Cys | Ile | Lys | Thr | Thr | Val | Glu | Asn | Glu | Leu | Pro | Pro | Pro | Glu |
| | | 220 | | | | | 225 | | | | | 230 | | | |
| AAT | ATA | GAA | GTC | AGT | GTC | CAA | AAT | CAG | AAC | TAT | GTT | CTT | AAA | TGG | GAT | 773 |
| Asn | Ile | Glu | Val | Ser | Val | Gln | Asn | Gln | Asn | Tyr | Val | Leu | Lys | Trp | Asp |
| | 235 | | | | | 240 | | | | | 245 | | | | |
| TAT | ACA | TAT | GCA | AAC | ATG | ACC | TTT | CAA | GTT | CAG | TGG | CTC | CAC | GCC | TTT | 821 |
| Tyr | Thr | Tyr | Ala | Asn | Met | Thr | Phe | Gln | Val | Gln | Trp | Leu | His | Ala | Phe |
| 250 | | | | | 255 | | | | | 260 | | | | | 265 |
| TTA | AAA | AGG | AAT | CCT | GGA | AAC | CAT | TTG | TAT | AAA | TGG | AAA | CAA | ATA | CCT | 869 |
| Leu | Lys | Arg | Asn | Pro | Gly | Asn | His | Leu | Tyr | Lys | Trp | Lys | Gln | Ile | Pro |
| | | | | 270 | | | | | 275 | | | | | 280 | |

```
GAC TGT GAA AAT GTC AAA ACT ACC CAG TGT GTC TTT CCT CAA AAC GTT        917
Asp Cys Glu Asn Val Lys Thr Thr Gln Cys Val Phe Pro Gln Asn Val
            285                 290                 295

TTC CAA AAA GGA ATT TAC CTT CTC CGC GTA CAA GCA TCT GAT GGA AAT        965
Phe Gln Lys Gly Ile Tyr Leu Leu Arg Val Gln Ala Ser Asp Gly Asn
        300                 305                 310

AAC ACA TCT TTT TGG TCT GAA GAG ATA AAG TTT GAT ACT GAA ATA CAA       1013
Asn Thr Ser Phe Trp Ser Glu Glu Ile Lys Phe Asp Thr Glu Ile Gln
    315                 320                 325

GCT TTC CTA CTT CCT CCA GTC TTT AAC ATT AGA TCC CTT AGT GAT TCA       1061
Ala Phe Leu Leu Pro Pro Val Phe Asn Ile Arg Ser Leu Ser Asp Ser
330                 335                 340                 345

TTC CAT ATC TAT ATC GGT GCT CCA AAA CAG TCT GGA AAC ACG CCT GTG       1109
Phe His Ile Tyr Ile Gly Ala Pro Lys Gln Ser Gly Asn Thr Pro Val
                350                 355                 360

ATC CAG GAT TAT CCA CTG ATT TAT GAA ATT ATT TTT TGG GAA AAC ACT       1157
Ile Gln Asp Tyr Pro Leu Ile Tyr Glu Ile Ile Phe Trp Glu Asn Thr
            365                 370                 375

TCA AAT GCT GAG AGA AAA ATT ATC GAG AAA AAA ACT GAT GTT ACA GTT       1205
Ser Asn Ala Glu Arg Lys Ile Ile Glu Lys Lys Thr Asp Val Thr Val
        380                 385                 390

CCT AAT TTG AAA CCA CTG ACT GTA TAT TGT GTG AAA GCC AGA GCA CAC       1253
Pro Asn Leu Lys Pro Leu Thr Val Tyr Cys Val Lys Ala Arg Ala His
    395                 400                 405

ACC ATG GAT GAA AAG CTG AAT AAA AGC AGT GTT TTT AGT GAC GCT GTA       1301
Thr Met Asp Glu Lys Leu Asn Lys Ser Ser Val Phe Ser Asp Ala Val
410                 415                 420                 425

TGT GAG AAA ACA AAA CCA GGA AAT ACC TCT AAA TGAGGTACC                 1343
Cys Glu Lys Thr Lys Pro Gly Asn Thr Ser Lys
                430                 435

(2) INFORMATION FOR SEQ ID NO:2:

(i) SEQUENCE CHARACTERISTICS:
        (A) LENGTH: 436 amino acids
        (B) TYPE: amino acid
        (D) TOPOLOGY: linear (ii) MOLECULE TYPE: protein (xi) SEQUENCE DESCRIPTION: SEQ ID NO:2:

Met Met Val Val Leu Leu Gly Ala Thr Thr Leu Val Leu Val Ala Val
 1               5                  10                  15

Gly Pro Trp Val Leu Ser Ala Ala Gly Gly Lys Asn Leu Lys Ser
             20                  25                  30

Pro Gln Lys Val Glu Val Asp Ile Ile Asp Asp Asn Phe Ile Leu Arg
         35                  40                  45

Trp Asn Arg Ser Asp Glu Ser Val Gly Asn Val Thr Phe Ser Phe Asp
     50                  55                  60

Tyr Gln Lys Thr Gly Met Asp Asn Trp Ile Lys Leu Ser Gly Cys Gln
 65                  70                  75                  80

Asn Ile Thr Ser Thr Lys Cys Asn Phe Ser Ser Leu Lys Leu Asn Val
                 85                  90                  95

Tyr Glu Glu Ile Lys Leu Arg Ile Arg Ala Glu Lys Glu Asn Thr Ser
             100                 105                 110

Ser Trp Tyr Glu Val Asp Ser Phe Thr Pro Phe Arg Lys Ala Gln Ile
         115                 120                 125

Gly Pro Pro Glu Val His Leu Glu Ala Glu Asp Lys Ala Ile Val Ile
     130                 135                 140
```

-continued

```
His Ile Ser Pro Gly Thr Lys Asp Ser Val Met Trp Ala Leu Asp Gly
145                 150                 155                 160

Leu Ser Phe Thr Tyr Ser Leu Leu Ile Trp Lys Asn Ser Ser Gly Val
                165                 170                 175

Glu Glu Arg Ile Glu Asn Ile Tyr Ser Arg His Lys Ile Tyr Lys Leu
            180                 185                 190

Ser Pro Glu Thr Thr Tyr Cys Leu Lys Val Lys Ala Ala Leu Leu Thr
        195                 200                 205

Ser Trp Lys Ile Gly Val Tyr Ser Pro Val His Cys Ile Lys Thr Thr
210                 215                 220

Val Glu Asn Glu Leu Pro Pro Glu Asn Ile Glu Val Ser Val Gln
225                 230                 235                 240

Asn Gln Asn Tyr Val Leu Lys Trp Asp Tyr Thr Tyr Ala Asn Met Thr
                245                 250                 255

Phe Gln Val Gln Trp Leu His Ala Phe Leu Lys Arg Asn Pro Gly Asn
            260                 265                 270

His Leu Tyr Lys Trp Lys Gln Ile Pro Asp Cys Glu Asn Val Lys Thr
        275                 280                 285

Thr Gln Cys Val Phe Pro Gln Asn Val Phe Gln Lys Gly Ile Tyr Leu
    290                 295                 300

Leu Arg Val Gln Ala Ser Asp Gly Asn Asn Thr Ser Phe Trp Ser Glu
305                 310                 315                 320

Glu Ile Lys Phe Asp Thr Glu Ile Gln Ala Phe Leu Leu Pro Pro Val
                325                 330                 335

Phe Asn Ile Arg Ser Leu Ser Asp Ser Phe His Ile Tyr Ile Gly Ala
            340                 345                 350

Pro Lys Gln Ser Gly Asn Thr Pro Val Ile Gln Asp Tyr Pro Leu Ile
        355                 360                 365

Tyr Glu Ile Ile Phe Trp Glu Asn Thr Ser Asn Ala Glu Arg Lys Ile
    370                 375                 380

Ile Glu Lys Lys Thr Asp Val Thr Val Pro Asn Leu Lys Pro Leu Thr
385                 390                 395                 400

Val Tyr Cys Val Lys Ala Arg Ala His Thr Met Asp Glu Lys Leu Asn
                405                 410                 415

Lys Ser Ser Val Phe Ser Asp Ala Val Cys Glu Lys Thr Lys Pro Gly
            420                 425                 430

Asn Thr Ser Lys
        435
```

(2) INFORMATION FOR SEQ ID NO:3:

(i) SEQUENCE CHARACTERISTICS:
        (A) LENGTH: 1755 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 27..1697

(xi) SEQUENCE DESCRIPTION: SEQ ID NO:3:

```
CTGCAGGGAT CTGCGGCGGC TCCCAG ATG ATG GTC GTC CTC CTG GGC GCG ACG        53
                      Met Met Val Val Leu Leu Gly Ala Thr
                      440                 445
```

```
ACC CTA GTG CTC GTC GCC GTG GGC CCA TGG GTG TTG TCC GCA GCC GCA      101
Thr Leu Val Leu Val Ala Val Gly Pro Trp Val Leu Ser Ala Ala Ala
            450                 455                 460

GGT GGA AAA AAT CTA AAA TCT CCT CAA AAA GTA GAG GTC GAC ATC ATA      149
Gly Gly Lys Asn Leu Lys Ser Pro Gln Lys Val Glu Val Asp Ile Ile
            465                 470                 475

GAT GAC AAC TTT ATC CTG AGG TGG AAC AGG AGC GAT GAG TCT GTC GGG      197
Asp Asp Asn Phe Ile Leu Arg Trp Asn Arg Ser Asp Glu Ser Val Gly
            480                 485                 490

AAT GTG ACT TTT TCA TTC GAT TAT CAA AAA ACT GGG ATG GAT AAT TGG      245
Asn Val Thr Phe Ser Phe Asp Tyr Gln Lys Thr Gly Met Asp Asn Trp
    495                 500                 505

ATA AAA TTG TCT GGG TGT CAG AAT ATT ACT AGT ACC AAA TGC AAC TTT      293
Ile Lys Leu Ser Gly Cys Gln Asn Ile Thr Ser Thr Lys Cys Asn Phe
510                 515                 520                 525

TCT TCA CTC AAG CTG AAT GTT TAT GAA GAA ATT AAA TTG CGT ATA AGA      341
Ser Ser Leu Lys Leu Asn Val Tyr Glu Glu Ile Lys Leu Arg Ile Arg
                530                 535                 540

GCA GAA AAA GAA AAC ACT TCT TCA TGG TAT GAG GTT GAC TCA TTT ACA      389
Ala Glu Lys Glu Asn Thr Ser Ser Trp Tyr Glu Val Asp Ser Phe Thr
            545                 550                 555

CCA TTT CGC AAA GCT CAG ATT GGT CCT CCA GAA GTA CAT TTA GAA GCT      437
Pro Phe Arg Lys Ala Gln Ile Gly Pro Pro Glu Val His Leu Glu Ala
            560                 565                 570

GAA GAT AAG GCA ATA GTG ATA CAC ATC TCT CCT GGA ACA AAA GAT AGT      485
Glu Asp Lys Ala Ile Val Ile His Ile Ser Pro Gly Thr Lys Asp Ser
575                 580                 585

GTT ATG TGG GCT TTG GAT GGT TTA AGC TTT ACA TAT AGC TTA CTT ATC      533
Val Met Trp Ala Leu Asp Gly Leu Ser Phe Thr Tyr Ser Leu Leu Ile
590                 595                 600                 605

TGG AAA AAC TCT TCA GGT GTA GAA GAA AGG ATT GAA AAT ATT TAT TCC      581
Trp Lys Asn Ser Ser Gly Val Glu Glu Arg Ile Glu Asn Ile Tyr Ser
            610                 615                 620

AGA CAT AAA ATT TAT AAA CTC TCA CCA GAG ACT ACT TAT TGT CTA AAA      629
Arg His Lys Ile Tyr Lys Leu Ser Pro Glu Thr Thr Tyr Cys Leu Lys
            625                 630                 635

GTT AAA GCA GCA CTA CTT ACG TCA TGG AAA ATT GGT GTC TAT AGT CCA      677
Val Lys Ala Ala Leu Leu Thr Ser Trp Lys Ile Gly Val Tyr Ser Pro
            640                 645                 650

GTA CAT TGT ATA AAG ACC ACA GTT GAA AAT GAA CTA CCT CCA CCA GAA      725
Val His Cys Ile Lys Thr Thr Val Glu Asn Glu Leu Pro Pro Pro Glu
655                 660                 665

AAT ATA GAA GTC AGT GTC CAA AAT CAG AAC TAT GTT CTT AAA TGG GAT      773
Asn Ile Glu Val Ser Val Gln Asn Gln Asn Tyr Val Leu Lys Trp Asp
670                 675                 680                 685

TAT ACA TAT GCA AAC ATG ACC TTT CAA GTT CAG TGG CTC CAC GCC TTT      821
Tyr Thr Tyr Ala Asn Met Thr Phe Gln Val Gln Trp Leu His Ala Phe
                690                 695                 700

TTA AAA AGG AAT CCT GGA AAC CAT TTG TAT AAA TGG AAA CAA ATA CCT      869
Leu Lys Arg Asn Pro Gly Asn His Leu Tyr Lys Trp Lys Gln Ile Pro
            705                 710                 715

GAC TGT GAA AAT GTC AAA ACT ACC CAG TGT GTC TTT CCT CAA AAC GTT      917
Asp Cys Glu Asn Val Lys Thr Thr Gln Cys Val Phe Pro Gln Asn Val
            720                 725                 730

TTC CAA AAA GGA ATT TAC CTT CTC CGC GTA CAA GCA TCT GAT GGA AAT      965
Phe Gln Lys Gly Ile Tyr Leu Leu Arg Val Gln Ala Ser Asp Gly Asn
        735                 740                 745

AAC ACA TCT TTT TGG TCT GAA GAG ATA AAG TTT GAT ACT GAA ATA CAA      1013
Asn Thr Ser Phe Trp Ser Glu Glu Ile Lys Phe Asp Thr Glu Ile Gln
750                 755                 760                 765
```

```
GCT TTC CTA CTT CCT CCA GTC TTT AAC ATT AGA TCC CTT AGT GAT TCA    1061
Ala Phe Leu Leu Pro Pro Val Phe Asn Ile Arg Ser Leu Ser Asp Ser
            770                 775                 780

TTC CAT ATC TAT ATC GGT GCT CCA AAA CAG TCT GGA AAC ACG CCT GTG    1109
Phe His Ile Tyr Ile Gly Ala Pro Lys Gln Ser Gly Asn Thr Pro Val
            785                 790                 795

ATC CAG GAT TAT CCA CTG ATT TAT GAA ATT ATT TTT TGG GAA AAC ACT    1157
Ile Gln Asp Tyr Pro Leu Ile Tyr Glu Ile Ile Phe Trp Glu Asn Thr
            800                 805                 810

TCA AAT GCT GAG AGA AAA ATT ATC GAG AAA AAA ACT GAT GTT ACA GTT    1205
Ser Asn Ala Glu Arg Lys Ile Ile Glu Lys Lys Thr Asp Val Thr Val
            815                 820                 825

CCT AAT TTG AAA CCA CTG ACT GTA TAT TGT GTG AAA GCC AGA GCA CAC    1253
Pro Asn Leu Lys Pro Leu Thr Val Tyr Cys Val Lys Ala Arg Ala His
830                 835                 840                 845

ACC ATG GAT GAA AAG CTG AAT AAA AGC AGT GTT TTT AGT GAC GCT GTA    1301
Thr Met Asp Glu Lys Leu Asn Lys Ser Ser Val Phe Ser Asp Ala Val
            850                 855                 860

TGT GAG AAA ACA AAA CCA GGA AAT ACC TCT AAA ATT TGG CTT ATA GTT    1349
Cys Glu Lys Thr Lys Pro Gly Asn Thr Ser Lys Ile Trp Leu Ile Val
            865                 870                 875

GGA ATT TGT ATT GCA TTA TTT GCT CTC CCG TTT GTC ATT TAT GCT GCG    1397
Gly Ile Cys Ile Ala Leu Phe Ala Leu Pro Phe Val Ile Tyr Ala Ala
            880                 885                 890

AAA CTC TTC TTG AGA TGC ATC AAT TAT GTC TTC TTT CCA TCA CTT AAA    1445
Lys Leu Phe Leu Arg Cys Ile Asn Tyr Val Phe Phe Pro Ser Leu Lys
            895                 900                 905

CCT TCT TCC AGT ATA GAT GAG TAT TTC TCT GAA CAG CCA TTG AAG AAT    1493
Pro Ser Ser Ser Ile Asp Glu Tyr Phe Ser Glu Gln Pro Leu Lys Asn
910                 915                 920                 925

CTT CTG CTT TCA ACT TCT GAG GAA CAA ATC GAA AAA TGT TTC ATA ATT    1541
Leu Leu Leu Ser Thr Ser Glu Glu Gln Ile Glu Lys Cys Phe Ile Ile
            930                 935                 940

GAA AAT ATA AGC ACA ATT GCT ACA GTA GAA GAA ACT AAT CAA ACT GAT    1589
Glu Asn Ile Ser Thr Ile Ala Thr Val Glu Glu Thr Asn Gln Thr Asp
            945                 950                 955

GAA GAT CAT AAA AAA TAC AGT TCC CAA ACT AGC CAA GAT TCA GGA AAT    1637
Glu Asp His Lys Lys Tyr Ser Ser Gln Thr Ser Gln Asp Ser Gly Asn
            960                 965                 970

TAT TCT AAT GAA GAT GAA AGC GAA AGT AAA ACA AGT GAA GAA CTA CAG    1685
Tyr Ser Asn Glu Asp Glu Ser Glu Ser Lys Thr Ser Glu Glu Leu Gln
975                 980                 985

CAG GAC TTT GTA TGACCAGAAA TGAACTGTGT CAAGTATAAG GTTTTTCAGC        1737
Gln Asp Phe Val
990

AGGAGTTACA CTGGTACC                                                 1755

(2) INFORMATION FOR SEQ ID NO:4:

(i) SEQUENCE CHARACTERISTICS:
        (A) LENGTH: 557 amino acids
        (B) TYPE: amino acid
        (D) TOPOLOGY: linear (ii) MOLECULE TYPE: protein (xi) SEQUENCE DESCRIPTION: SEQ ID NO:4:

Met Met Val Val Leu Leu Gly Ala Thr Thr Leu Val Leu Val Ala Val
 1               5                  10                  15

Gly Pro Trp Val Leu Ser Ala Ala Ala Gly Gly Lys Asn Leu Lys Ser
                20                  25                  30
```

-continued

```
Pro Gln Lys Val Glu Val Asp Ile Ile Asp Asp Asn Phe Ile Leu Arg
         35                  40                  45

Trp Asn Arg Ser Asp Glu Ser Val Gly Asn Val Thr Phe Ser Phe Asp
     50                  55                  60

Tyr Gln Lys Thr Gly Met Asp Asn Trp Ile Lys Leu Ser Gly Cys Gln
 65                  70                  75                  80

Asn Ile Thr Ser Thr Lys Cys Asn Phe Ser Ser Leu Lys Leu Asn Val
                 85                  90                  95

Tyr Glu Glu Ile Lys Leu Arg Ile Arg Ala Glu Lys Glu Asn Thr Ser
                100                 105                 110

Ser Trp Tyr Glu Val Asp Ser Phe Thr Pro Phe Arg Lys Ala Gln Ile
            115                 120                 125

Gly Pro Pro Glu Val His Leu Glu Ala Glu Asp Lys Ala Ile Val Ile
        130                 135                 140

His Ile Ser Pro Gly Thr Lys Asp Ser Val Met Trp Ala Leu Asp Gly
145                 150                 155                 160

Leu Ser Phe Thr Tyr Ser Leu Leu Ile Trp Lys Asn Ser Ser Gly Val
                165                 170                 175

Glu Glu Arg Ile Glu Asn Ile Tyr Ser Arg His Lys Ile Tyr Lys Leu
            180                 185                 190

Ser Pro Glu Thr Thr Tyr Cys Leu Lys Val Lys Ala Ala Leu Leu Thr
        195                 200                 205

Ser Trp Lys Ile Gly Val Tyr Ser Pro Val His Cys Ile Lys Thr Thr
    210                 215                 220

Val Glu Asn Glu Leu Pro Pro Pro Glu Asn Ile Glu Val Ser Val Gln
225                 230                 235                 240

Asn Gln Asn Tyr Val Leu Lys Trp Asp Tyr Thr Tyr Ala Asn Met Thr
                245                 250                 255

Phe Gln Val Gln Trp Leu His Ala Phe Leu Lys Arg Asn Pro Gly Asn
            260                 265                 270

His Leu Tyr Lys Trp Lys Gln Ile Pro Asp Cys Glu Asn Val Lys Thr
        275                 280                 285

Thr Gln Cys Val Phe Pro Gln Asn Val Phe Gln Lys Gly Ile Tyr Leu
    290                 295                 300

Leu Arg Val Gln Ala Ser Asp Gly Asn Asn Thr Ser Phe Trp Ser Glu
305                 310                 315                 320

Glu Ile Lys Phe Asp Thr Glu Ile Gln Ala Phe Leu Leu Pro Pro Val
                325                 330                 335

Phe Asn Ile Arg Ser Leu Ser Asp Ser Phe His Ile Tyr Ile Gly Ala
            340                 345                 350

Pro Lys Gln Ser Gly Asn Thr Pro Val Ile Gln Asp Tyr Pro Leu Ile
        355                 360                 365

Tyr Glu Ile Ile Phe Trp Glu Asn Thr Ser Asn Ala Glu Arg Lys Ile
    370                 375                 380

Ile Glu Lys Lys Thr Asp Val Thr Val Pro Asn Leu Lys Pro Leu Thr
385                 390                 395                 400

Val Tyr Cys Val Lys Ala Arg Ala His Thr Met Asp Glu Lys Leu Asn
                405                 410                 415

Lys Ser Ser Val Phe Ser Asp Ala Val Cys Glu Lys Thr Lys Pro Gly
            420                 425                 430

Asn Thr Ser Lys Ile Trp Leu Ile Val Gly Ile Cys Ile Ala Leu Phe
        435                 440                 445
```

```
Ala Leu Pro Phe Val Ile Tyr Ala Ala Lys Leu Phe Leu Arg Cys Ile
    450                 455                 460

Asn Tyr Val Phe Phe Pro Ser Leu Lys Pro Ser Ser Ile Asp Glu
465                 470                 475                 480

Tyr Phe Ser Glu Gln Pro Leu Lys Asn Leu Leu Ser Thr Ser Glu
                485                 490                 495

Glu Gln Ile Glu Lys Cys Phe Ile Ile Glu Asn Ile Ser Thr Ile Ala
            500                 505                 510

Thr Val Glu Glu Thr Asn Gln Thr Asp Glu Asp His Lys Lys Tyr Ser
                515                 520                 525

Ser Gln Thr Ser Gln Asp Ser Gly Asn Tyr Ser Asn Glu Asp Glu Ser
            530                 535                 540

Glu Ser Lys Thr Ser Glu Glu Leu Gln Gln Asp Phe Val
545                 550                 555
```

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:5:

CCGGCTGCAG GGATCTGCGG CGGCTCCCAG          30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:6:

CCGGTACCAG TGTAACTCCT GCTGAAAAAC          30

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:7:

CCGGTACCTC ATTTAGAGGT ATTTCCTGG          29

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:8:

CCGGTACCTC ACTCACATAC AGCGTCACT                29

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:9:

CCGGTACCTC AAGGCGTGTT TCCAGACTG                29

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:10:

CCGGTACCTC ATTTGAGGAA AGACACACTG               30

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:11:

CCGGTACCTC ATAGACAATA AGTAGTCTC                29

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:12:

ACTGTGGCTG CACCATCTGT CTTCA                    25

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:13:

GACCGGTACC TCCCTCTAAC ACTCTCCC                 28

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:14:

```
TTTAGAGGTA TTTCCTGGTT TTGTTTTCTC                                    30
```

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:15:

```
CTCACATACA GCGACACTAA AAACACTGCT                                    30
```

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:16:

```
AGGCGTGTTT CCAGACTGTT TTGGAGCACC                                    30
```

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:17:

```
GCCTCCACCA AGGGCCCATC GGTCTTCCCC                                    30
```

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:18:

```
GACCGGTACC ACTCATTTAC CCGGAGACAG                                    30
```

(2) INFORMATION FOR SEQ ID NO:19:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:19:

GGTGGAAAAA ATCTAAAATC TCCTCAAAAA G               31

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:20:

CCGGTACCCT ACTCACATAC AGCGTCACT                29

(2) INFORMATION FOR SEQ ID NO:21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:21:

GGAAAAAATC TAAAATCTCC TCAAAAAG                 28